United States Patent
Ben-David et al.

(10) Patent No.: US 10,548,498 B2
(45) Date of Patent: *Feb. 4, 2020

(54) DETECTION AND MONITORING USING HIGH FREQUENCY ELECTROGRAM ANALYSIS

(71) Applicant: BSP Biological Signal Processing Ltd., Tel-Aviv (IL)

(72) Inventors: Tamir Ben-David, Tel-Aviv (IL); Yair Granot, Modiln (IL); Amir Beker, Rosh HaAyin (IL)

(73) Assignee: BSP Biological Signal Processing Ltd., Tel-Aviv (IL)

( * ) Notice: Subject to any disclaimer, the term of this patent is extended or adjusted under 35 U.S.C. 154(b) by 413 days.

This patent is subject to a terminal disclaimer.

(21) Appl. No.: 14/985,488

(22) Filed: Dec. 31, 2015

(65) Prior Publication Data

US 2016/0113533 A1 Apr. 28, 2016

Related U.S. Application Data

(63) Continuation-in-part of application No. 14/734,032, filed on Jun. 9, 2015, now Pat. No. 9,254,094, which
(Continued)

(51) Int. Cl.
*A61B 5/042* (2006.01)
*A61B 5/046* (2006.01)
(Continued)

(52) U.S. Cl.
CPC ............ *A61B 5/042* (2013.01); *A61B 5/0245* (2013.01); *A61B 5/02405* (2013.01);
(Continued)

(58) Field of Classification Search
CPC ... A61B 5/02405; A61B 5/0245; A61B 5/042; A61B 5/046; A61B 5/0464;
(Continued)

(56) References Cited

U.S. PATENT DOCUMENTS 4,422,459 A  12/1983  Simson
5,046,504 A   9/1991  Albert et al.
(Continued)

FOREIGN PATENT DOCUMENTS

CN     1084044      3/1994
WO  WO 2005/104937  11/2005

OTHER PUBLICATIONS

Applicant-Initiated Interview Summary dated Nov. 12, 2014 From the U.S. Patent and Trademark Office Re. U.S. Appl. No. 14/299,331.
(Continued)

*Primary Examiner* — Christopher Koharski
*Assistant Examiner* — Adreanne A. Arnold

(57) ABSTRACT

An implantable device for analyzing a high frequency (HF) electrogram signal received from subcutaneous, above-rib pickup locations, the device including an implantable electrode for use inside a living body, and a can for subcutaneous implantation, the can including a signal pickup configured to pick up an electrogram signal including a high frequency (HF) component, a signal filter connected to the signal pickup and configured to measure a high frequency (HF) component from the electrogram signal, and an analyzer for analyzing the HF component of the electrogram signal, wherein the analyzer is configured to analyze at least one time-varying parameter of the HF component of the electrogram signal, and the signal filter is configured to measure the electrogram signal by using a signal picked up from at least two pickup locations which are both subcutaneous and above-rib. Related apparatus and methods are also described.

20 Claims, 21 Drawing Sheets

Related U.S. Application Data is a continuation-in-part of application No. 14/299,331, filed on Jun. 9, 2014, now Pat. No. 9,167,980.

(60) Provisional application No. 61/832,863, filed on Jun. 9, 2013.

(51) Int. Cl.

| | |
|---|---|
| *A61N 1/365* | (2006.01) |
| *A61B 5/0472* | (2006.01) |
| *A61B 5/0464* | (2006.01) |
| *A61B 5/024* | (2006.01) |
| *A61B 5/00* | (2006.01) |
| *A61B 5/0245* | (2006.01) |
| *A61N 1/37* | (2006.01) |
| *A61B 5/08* | (2006.01) |

(52) U.S. Cl.
CPC ............ *A61B 5/046* (2013.01); *A61B 5/0464* (2013.01); *A61B 5/0472* (2013.01); *A61B 5/686* (2013.01); *A61N 1/36514* (2013.01); *A61B 5/0816* (2013.01); *A61B 5/4836* (2013.01); *A61B 2560/0209* (2013.01); *A61N 1/3702* (2013.01)

(58) Field of Classification Search
CPC ... A61B 5/0472; A61B 5/0816; A61B 5/4836; A61B 5/686; A61B 2560/0209; A61N 1/36514; A61N 1/3702
USPC ................................. 600/509, 516, 517, 521
See application file for complete search history.

(56) References Cited

U.S. PATENT DOCUMENTS

| | | | |
|---|---|---|---|
| 5,117,833 A | 6/1992 | Albert et al. | |
| 5,348,020 A | 9/1994 | Hutson | |
| 5,404,877 A | 4/1995 | Nolan et al. | |
| 5,655,540 A | 8/1997 | Segobin | |
| 5,836,982 A | 11/1998 | Mühlenberg et al. | |
| 5,954,664 A | 9/1999 | Seegobin | |
| 6,128,526 A | 10/2000 | Stadler et al. | |
| 6,600,949 B1 | 7/2003 | Turcott | |
| 7,113,820 B2 | 9/2006 | Schlegel et al. | |
| 7,151,957 B2 | 12/2006 | Beker et al. | |
| 7,239,988 B2 | 7/2007 | Hasson et al. | |
| 7,386,340 B2 | 7/2008 | Schlegel et al. | |
| 7,412,283 B2 | 8/2008 | Ginzburg et al. | |
| 7,539,535 B1 | 5/2009 | Schlegel et al. | |
| 8,538,510 B2 | 9/2013 | Toledo et al. | |
| 8,626,275 B1 | 1/2014 | Amit et al. | |
| 8,706,201 B2 | 4/2014 | Beker et al. | |
| 9,167,980 B2* | 10/2015 | Ben-David | A61B 5/04015 |
| 9,254,094 B2* | 2/2016 | Ben-David | A61B 5/02405 |
| 2005/0177049 A1 | 8/2005 | Hardahl et al. | |
| 2006/0074451 A1 | 4/2006 | Chen et al. | |
| 2006/0247686 A1 | 11/2006 | Girouard et al. | |
| 2007/0146189 A1 | 6/2007 | Wesselink et al. | |
| 2007/0233196 A1* | 10/2007 | Stadler | A61N 1/3621 607/4 |
| 2008/0167567 A1 | 7/2008 | Bashour et al. | |
| 2008/0194978 A1* | 8/2008 | Beker | A61B 5/0452 600/516 |
| 2009/0318820 A1 | 12/2009 | Toledo et al. | |
| 2010/0217144 A1 | 8/2010 | Brian | |
| 2011/0190647 A1 | 8/2011 | Helfenbein et al. | |
| 2015/0257669 A1 | 9/2015 | Ben-David et al. | |
| 2015/0272463 A1 | 10/2015 | Ben-David et al. | |

OTHER PUBLICATIONS

European Search Report and the European Search Opinion dated Nov. 6, 2015 From the European Patent Office Re. Application No. 15171155.3.
Official Action dated Sep. 3, 2014 From the U.S. Patent and Trademark Office Re. U.S. Appl. No. 14/299,331.
Official Action dated Mar. 12, 2015 From the U.S. Patent and Trademark Office Re. U.S. Appl. No. 14/299,331.
Moody et al. "Derivation of Respiratory Signals From Multi-Lead ECGs", Computers in Cardiology, 12: 113-116, 1985.
Communication Pursuant to Article 94(3) EPC dated Dec. 21, 2018 From the European Patent Office Re. Application No. 15171155.3. (6 Pages).

* cited by examiner

DETECTION AND MONITORING USING HIGH FREQUENCY ELECTROGRAM ANALYSIS

RELATED APPLICATIONS

This application is a Continuation-In-Part (CIP) of U.S. patent application Ser. No. 14/734,032 filed on Jun. 9, 2015, now U.S. Pat. No. 9,254,094, which is a Continuation-In-Part (CIP) of U.S. patent application Ser. No. 14/299,331 filed on Jun. 9, 2014, now U.S. Pat. No. 9,167,980, which claims the benefit of priority of U.S. Provisional Patent Application No. 61/832,863 filed Jun. 9, 2013. The contents of the above applications are all incorporated by reference as if fully set forth herein in their entirety.

FIELD AND BACKGROUND OF THE INVENTION

The present invention, in some embodiments thereof, relates to an apparatus and method for detecting myocardial ischemia using analysis of high frequency components of an electrocardiogram and/or of a cardiac electrogram, and, more particularly, but not exclusively, to an implantable such apparatus and method.

An electrocardiogram (ECG) is used to measure rate and regularity of heartbeats, as well as a size and position of heart chambers, presence of damage to the heart, and effects of drugs or devices used to regulate the heart.

Usually two or more electrodes are used for electrocardiogram (ECG) measurement. The electrodes can be combined into a number of pairs. Output from a pair of electrodes is known as a lead.

An ECG is a common way to measure and diagnose abnormalities in electrical activity of the cardiac muscle and abnormal rhythms of the heart, particularly abnormalities caused by damage to conductive tissue that carries electrical signals, or abnormal rhythms caused by electrolyte imbalances. In a condition of myocardial infarction (MI), the ECG can identify if the heart muscle has been damaged and sometime also indicate the location of damage, though not all areas of the heart are covered.

A typical ECG device detects and amplifies tiny electrical changes on a subject's skin which are caused when a heart muscle depolarizes and subsequently repolarizes during each heartbeat. At rest, each cardiac muscle cell is negatively charged, causing a membrane potential across its cell membrane. A cell's activation phase commences with depolarization, initiated by an influx of positive cations, Na+ and Ca++, and decreasing the absolute value of the negative charge towards zero. The depolarization activates mechanical mechanisms in the cardiac muscle cell which causes contraction in the cardiac muscle. During each heart cycle, a healthy heart has an orderly progression as a wave of depolarization which is triggered by cells in the sinoatrial node spreads out through the atrium, then passes through the atrioventricular node and finally spreads over the ventricles. The progression is detected as waveforms in the recorded potential difference (or voltage) between electrodes placed on either side of the heart and may be displayed as a graph either on screen or on paper. The produced signal reflects the electrical activity of the heart, and different leads express more clearly different parts of the heart muscle.

A typical ECG trace of the cardiac cycle (heartbeat) consists of a P wave, a QRS complex, a T wave, and a U wave which is normally visible in 50% to 75% of ECG traces. A baseline voltage of the electrocardiogram is known as the isoelectric line. Typically, the isoelectric line is measured as the portion of the ECG trace following the T wave and preceding the next P wave.

A standard ECG traces usually filters out high frequency (HF) components, typically above 100 Hz. In some commercial implementations, lower thresholds such as 75 Hz or even 50 Hz are used for the low-pass filtering process. In general, the noise level is such that high frequency components, above 150 Hz, which are typically measured in micro-volts, are not reliably isolated from a single ECG trace and identified or measured. In order to measure and process high frequency components, one typically needs to use signal-to-noise enhancement schemes such as filtering and averaging.

An article by George B. Moody, Roger G. Mark, Andrea Zoccola and Sara Mantero titled "Derivation of Respiratory Signals from Multi-lead ECGs", published in Computers in Cardiology 1985, vol. 12, pp. 113-116, Washington, D.C.: IEEE Computer Society Press, describes a signal-processing technique which derives respiratory waveforms from ordinary ECGs, permitting detection of respiratory efforts.

Additional background art includes:
U.S. Pat. No. 8,706,201 to Beker et al.
U.S. Pat. No. 8,626,275 to Amit et al.
U.S. Pat. No. 8,538,510 to Toledo et al.
U.S. Pat. No. 7,539,535 to Schlegel et al.
U.S. Pat. No. 7,412,283 to Ginzburg et al.
U.S. Pat. No. 7,386,340 to Schlegel et al.
U.S. Pat. No. 7,239,988 to Hasson et al.
U.S. Pat. No. 7,151,957 to Beker et al.
U.S. Pat. No. 7,113,820 to Schlegel et al.
U.S. Pat. No. 6,600,949 to Turcott.
U.S. Pat. No. 6,128,526 to Stadler et al.
U.S. Pat. No. 5,954,664 to Seegobin.
U.S. Pat. No. 5,655,540 to Seegobin et al.
U.S. Pat. No. 5,404,877 to Nolan el al.
U.S. Pat. No. 5,348,020 to Hutson.
U.S. Pat. No. 5,117,833 to Albert et al.
U.S. Pat. No. 5,046,504 to Albert et al.
U.S. Pat. No. 4,422,459 to Simpson.
U.S. Patent Publication number 2005/0177049 to Hardahl et al.
U.S. Patent Publication number 2006/0074451 to Chen et al.
PCT Patent Application Publication WO 2005/104937.

The disclosures of all references mentioned above and throughout the present specification, as well as the disclosures of all references mentioned in those references, are hereby incorporated herein by reference.

SUMMARY OF THE INVENTION

An aspect of some embodiments of the invention relates to electrogram signals gathered from implanted electrodes being stronger than electrocardiogram signals gathered from electrodes attached to a subject's skin.

An aspect of some embodiments of the invention relates to the stronger, and potentially higher signal-to-noise (S/N) ratio, electrogram signals being synergistically conducive to analyzing high frequency (HF) electrogram signals, which are weaker, and potentially lower S/N ratio, when gathered from electrodes attached to a subject's skin. In the present specification and claims the term HF electrogram signals refers to components of an electrogram at frequencies above 100 Hz.

The term "electrocardiogram" is typically used in the art for a signal collected by a sensor placed on a patient's skin.

The term "electrogram" is typically used in the art for a signal collected by a sensor placed elsewhere, such as, by way of a non-limiting example, subcutaneously. The term "electrogram" is used throughout the present specification and claims interchangeably with the term "electrocardiogram".

Subcutaneous literally means below a skin. In various example embodiments subcutaneous may mean, by way of some non-limiting examples, below the skin and not too deep, and/or below the skin and not deeper than 1 centimeter below the skin, and/or below the skin and not beneath muscle.

In some embodiments, subcutaneous implantation is less invasive than deeper implants.

An aspect of some embodiments of the invention relates to saving power in an implanted device by gathering and/or analyzing electrogram signals only during a specific fraction of time, potentially lengthening duration of operation between possible battery charging and/or battery replacement.

An aspect of some embodiments of the invention relates to saving power in an implanted device by gathering and/or analyzing a high-frequency portion of electrogram signals only during a specific fraction of time, potentially lengthening duration of operation between possible battery charging and/or battery replacement.

An aspect of some embodiments of the invention relates to saving power in an implanted device by gathering and/or analyzing a low-frequency portion of electrogram signals only during a specific fraction of time, potentially lengthening duration of operation between possible battery charging and/or battery replacing.

An aspect of some embodiments of the invention relates to electrogram signals gathered from implanted electrodes enabling placing the electrodes at locations physiologically different than only electrodes attached to a subject's skin An aspect of some embodiments of the invention relates to electrogram signals gathered from the can of an implanted apparatus, which saves in a total number of implanted electrodes.

An aspect of some embodiments of the invention relates to electrogram signals gathered from electrodes located near to a known and/or to a suspected partial or complete occlusion in a blood vessel. The electrogram signal is optionally measured proximally and distally from the occlusion, and High frequency ECG values of the signal are optionally compared.

According to an aspect of some embodiments of the present invention there is provided a method for analyzing a high frequency (HF) electrogram signal including (a) providing at least one electrogram signal from an electrode located within a subject's body, (b) measuring the electrogram signal at a high frequency during a specific segment of a cardiac cycle, generating a HF electrogram signal, and (c) having a computer measure at least one time-varying parameter of the HF electrogram signal.

According to some embodiments of the invention, further including (d) having the computer detect a change in the time-varying parameter in comparison to a baseline value of the time-varying parameter, and (e) having the computer generate an alert based, at least in part, on the detection.

According to some embodiments of the invention, the measuring the electrogram signal at a high frequency during a specific segment of a cardiac cycle, generating a HF electrogram signal is performed such that a plurality of segments of the cardiac cycle are measured, and a plurality of the at least one time-varying parameter of the HF electrogram signal are measured, for the plurality of segments of the cardiac cycle.

According to some embodiments of the invention, a duration of the specific segment of a cardiac cycle is less than 40% of a duration of a full cardiac cycle.

According to some embodiments of the invention, the baseline value of the time-varying parameter is based on an average of the value of the time-varying parameter belonging to a specific category.

According to some embodiments of the invention, further including simultaneously measuring at least two time-varying parameters of the HF electrogram signal.

According to some embodiments of the invention, the specific segment of the cardiac cycle includes a QRS complex.

According to some embodiments of the invention, the specific segment of the cardiac cycle includes an interval selected from a group which consists of a P wave interval, and a T wave interval.

According to some embodiments of the invention, the measuring of the electrogram signal at a high frequency during a specific segment of a cardiac cycle includes not measuring the electrogram signal at a high frequency during another segment of the cardiac cycle.

According to some embodiments of the invention, the computer detects a change in the time-varying parameter by comparing an HF electrogram signal associated with a low heart rate to an HF electrogram signal associated with a higher heart rate.

According to some embodiments of the invention, the higher heart rate is at least 20% higher than the low heart rate. This figure of 20% is optionally a dynamically changeable parameter.

According to some embodiments of the invention the higher heart rate is optionally set to be 40% higher, 60%, 100% and even 200% greater than a minimal heart rate.

According to some embodiments of the invention the higher heart rate is optionally set in terms of a percentage of a maximal heart rate recommended, which is, by way of a non-limiting example, 220 minus a patient's age. In such embodiments values indicative of the higher heart rate are optionally in a range between 60-100% of the maximal heart rate.

According to some embodiments of the invention a value of a heart rate change is optionally preset by a physician according to a patient physical condition, such as age, sex, medical history, and historical heart rate patterns.

In some embodiments a wireless communication unit is included in an implantable device, such that an operator, typically a physician, can change parameters of the device using a programmer unit.

According to some embodiments of the invention a value of a heart rate change is optionally learned by a learning mechanism which optimizes the value to reduce false positive detection of cardiac conditions. The learning is optionally done during an evaluation period in which the device learns a patient's signal patterns and sets the value accordingly.

In some embodiments, an evaluation period is included, when a patient is optionally monitored by medical supervision. The evaluation period is optionally a few days when the patient has an in-hospital evaluation, or a few weeks when the patient is monitored in an out-of-hospital scenario. During this period, changes of the HF signal as a function of HR are optionally evaluated, and optionally serve as a reference for future evaluation. The monitoring potentially provides an indication if there are ischemic episodes during the evaluation period. In some cases, during an evaluation period, no significant events occur, and in some cases there is a change of the HF signal as a function of HR even in non ischemic scenarios. Such changes are optionally taken into account to reduce false positive detection.

According to some embodiments of the invention, the sampling of the electrogram signal at a high frequency includes sampling the electrogram signal at a high frequency during a specific segment of a breathing cycle.

According to some embodiments of the invention, the electrogram signal is measured between an electrode which is placed in a heart chamber and an electrode which is placed outside the heart chamber.

According to some embodiments of the invention, the electrogram signal is measured between an electrode which is placed in a first heart chamber and an electrode which is placed in a second heart chamber.

According to some embodiments of the invention, further including aligning and averaging a plurality of HF electrogram signals.

According to some embodiments of the invention, the aligning includes synchronization of HF electrogram signals based, at least in part, on a pacing signal.

According to some embodiments of the invention, the comparison includes comparing a value of the time-varying parameter of the HF electrogram signal and a baseline value of the time-varying parameter of the HF electrogram signal at different instances of similar heart rate values.

According to some embodiments of the invention, the time-varying parameter includes at least one selected from a group including an RMS level of the HF electrogram signal, a function of the RMS levels of the HF electrogram signal measured at a specific portion of a cardiac cycle, an envelope of the HF electrogram signal, a function of the envelope of the HF electrogram signal measured at a specific portion of a cardiac cycle, a width of the envelope of the HF electrogram signal, an area of a reduced amplitude zone (RAZ) of the HF electrogram signal, and an area of a RAZ in the envelope of the HF electrogram signal.

According to some embodiments of the invention, the alert is an alert indicating a condition selected from a group consisting of ischemia and other cardiac related events.

According to some embodiments of the invention, the specific segment of the cardiac cycle includes a P wave interval, and further including (d) having the computer detect a change in the time-varying parameter in comparison to a baseline value of the time-varying parameter, and (e) having the computer generate an alert indicating onset of atrial fibrillation based, at least in part, on the detection.

According to an aspect of some embodiments of the present invention there is provided IPG (implantable pulse generator) apparatus for analyzing a high frequency (HF) electrogram signal including an electrode for use inside a living body, a signal pickup configured to pick up an electrogram signal including a high frequency (HF) component, a measurement unit for measuring a high frequency (HF) component from the electrogram signal during a specific segment of a cardiac cycle, and an analyzer for analyzing the HF component of the electrogram signal, wherein the signal pickup, the measurement unit and the analyzer are included within an implantable container, and the analyzer is configured to measure at least one time-varying parameter of the HF electrogram signal.

According to some embodiments of the invention, the analyzer is configured to detect a change in the time-varying parameter in comparison to a baseline value of the time-varying parameter.

According to some embodiments of the invention, the analyzer is adapted to receive a synchronization signal from a pacing unit in the apparatus.

According to an aspect of some embodiments of the present invention there is provided a method for analyzing a high frequency (HF) electrogram signal including (a) providing at least one electrogram signal from an electrode located within a subject's body, (b) measuring the electrogram signal at a high frequency during a specific segment of a cardiac cycle, generating a HF electrogram signal, (c) having a computer measure at least one time-varying parameter of the HF electrogram signal, (d) having a computer detect a change in the time-varying parameter in comparison to a baseline value of the time-varying parameter, and (e) having the computer generate an alert based, at least in part, on the detection.

According to some embodiments of the invention, the measuring the electrogram signal at a high frequency during a specific segment of a cardiac cycle, generating a HF electrogram signal is performed such that a plurality of segments of the cardiac cycle are measured, and a plurality of the at least one time-varying parameter of the HF electrogram signal are measured, for the plurality of segments of the cardiac cycle.

According to some embodiments of the invention, a duration of the specific segment of a cardiac cycle is less than 50% of a duration of a full cardiac cycle.

According to some embodiments of the invention, the alert is sent to a cardiac pacing device.

According to some embodiments of the invention, the baseline value of the time-varying parameter is an average of the value of the time-varying parameter measured previously under similar conditions.

According to some embodiments of the invention, further including measuring at least two time-varying parameters of the HF electrogram signal, having the computer compare the two or more time-varying parameters of the HF electrogram signal, having the computer generate an alert based, at least in part, on the comparison.

According to some embodiments of the invention, the specific segment of the cardiac cycle is a QRS complex. According to some embodiments of the invention, the specific segment of the cardiac cycle is selected from a group which consists of a P wave interval, and a T wave interval.

According to some embodiments of the invention, the measuring of the electrogram signal at a high frequency during a specific segment of a cardiac cycle includes not measuring the electrogram signal at a high frequency during another segment of the cardiac cycle.

According to some embodiments of the invention, the measuring of the electrogram signal at a high frequency during a specific segment of a cardiac cycle further includes measuring the electrogram signal at a lower frequency during another segment of the cardiac cycle.

According to some embodiments of the invention, the high frequency is greater than 100 Hz and the lower frequency is lower than 150 Hz. According to some embodiments of the invention, the high frequency is greater than 150 Hz and the lower frequency is lower than 100 Hz.

According to some embodiments of the invention, detecting the segment of the cardiac cycle includes detecting atrial depolarization in the electrogram signal.

According to some embodiments of the invention, the sampling of the electrogram signal at a high frequency includes sampling the electrogram signal at a high frequency during a specific segment of a breathing cycle.

According to some embodiments of the invention, detecting the segment of the breathing cycle includes measuring amplitude of a QRS complex of a low frequency electrogram.

According to some embodiments of the invention, detecting the segment of the breathing cycle includes measuring a duration of a cardiac cycle.

According to some embodiments of the invention, the electrogram signal is measured between two electrodes which are placed both in the same heart chamber. According to some embodiments of the invention, the electrogram signal is measured between an electrode which is placed in a heart chamber and an electrode which is placed outside the heart chamber. According to some embodiments of the invention, the electrogram signal is measured between an electrode which is placed in a first heart chamber and an electrode which is placed in a second heart chamber. According to some embodiments of the invention, the electrogram signal is measured between an electrode which is placed touching a heart and an electrode which is electrically coupled to a device can.

According to some embodiments of the invention, the electrogram signal is measured between two locations adjacent to a heart, opening at least a 90 degree angle relative to a direction toward a center of mass of the heart.

According to some embodiments of the invention, the electrogram signal is measured between a first intracardiac electrode and a second epicardiac electrode. According to some embodiments of the invention, the electrogram signal is measured between a first intracardiac electrode and a second epicardiac electrode spaced apart to pick up signals from a small part of the heart.

According to some embodiments of the invention, further including aligning a plurality of HF electrogram signals to each other.

According to some embodiments of the invention, the aligning includes detecting a time of onset of depolarization of the electrogram of single electrode placed in the heart.

According to some embodiments of the invention, the aligning includes detecting a time of onset of depolarization of the electrogram of single electrode placed in the right cardiac atrium.

According to some embodiments of the invention, the comparison includes comparing a value of the time-varying parameter of the HF electrogram signal and a baseline value of the time-varying parameter of the HF electrogram signal at different instances of similar heart rate values.

According to some embodiments of the invention, the time-varying parameter includes at least one selected from a group including an RMS level of the HF electrogram signal, a function of the RMS levels of the HF electrogram signal measured at a specific portion of a cardiac cycle, an envelope of the HF electrogram signal, a function of the envelope of the HF electrogram signal measured at a specific portion of a cardiac cycle, a width of the envelope of the HF electrogram signal, an area of a reduced amplitude zone (RAZ) of the HF electrogram signal, and an area of a RAZ in the envelope of the HF electrogram signal.

According to some embodiments of the invention, the alert includes differentiating between ventricular tachycardia and supraventricular tachycardia.

According to an aspect of some embodiments of the present invention there is provided an implantable device for analyzing a high frequency (HF) electrogram signal including an implantable electrode for use inside a living body, a signal pickup configured to pick up an electrogram signal including a high frequency (HF) component, a signal filter connected to the signal pickup and configured to measure a high frequency (HF) component from the electrogram signal only during a specific portion of a cardiac cycle, and an analyzer for analyzing the HF component of the electrogram signal, wherein the signal pickup, the signal filter and the analyzer are included within an implantable container, and the analyzer is configured to analyze at least one time-varying parameter of the HF component of the electrogram signal, and the signal filter is configured to measure the electrogram signal by using a signal picked up from at least one electrode selected from a group consisting of (a) an intracardiac electrode, (b) a subcutaneous electrode, (c) a can of the implanted device, (d) a combination of two of the above.

According to some embodiments of the invention, the specific portion of the cardiac cycle includes at least part of a specific segment of the cardiac cycle, the specific segment of the cardiac cycle being one of a group consisting of a P segment, a Q segment, an R segment, an S segment, a T segment, and a QRS complex segment.

According to some embodiments of the invention, the signal filter is arranged for measuring an electrogram signal only during a specific portion of a cardiac cycle.

According to some embodiments of the invention, the signal filter is arranged to start measuring the electrogram signal a specific period of time following a synchronizing pacing signal.

According to some embodiments of the invention, the signal filter is arranged to start measuring the electrogram signal based, at least in part, on detecting a specific point in a low-frequency electrogram signal. According to some embodiments of the invention, the signal filter is arranged to stop measuring the electrogram signal based, at least in part, on detecting, in a low-frequency portion of the electrogram signal, a specific segment of the cardiac cycle.

According to some embodiments of the invention, the analyzer is configured to detect a change in the time-varying parameter in comparison to a baseline value of the time-varying parameter.

According to some embodiments of the invention, the specific segment of the cardiac cycle is a P segment, and the analyzer is configured to provide indication of atrial arrhythmia, and further including a pacing unit for manipulating a pacing rate, based on the indication, to overcome the atrial arrhythmia.

According to some embodiments of the invention, the signal filter for measuring a high frequency (HF) component from the electrogram signal is arranged to measure the electrogram signal at a frequency greater than 500 Hz.

According to some embodiments of the invention, the pacing unit is arranged to manipulate the pacing rate to overcome the atrial arrhythmia by increasing the pacing rate and subsequently decreasing the pacing rate.

According to some embodiments of the invention, the specific segment of the cardiac cycle is a QRS complex, and the analyzer is configured to provide indication of onset of an ischemic event, and further including a pacing unit arranged to manipulate a pacing rate, based on the indication, to overcome the onset of the ischemic event by reducing the pacing rate.

According to an aspect of some embodiments of the present invention there is provided a method for analyzing a high frequency (HF) electrogram signal including (a)

providing at least one electrogram signal from an electrode located within a subject's body, (b) measuring the electrogram signal at a high frequency only during a specific portion of a cardiac cycle, generating a HF electrogram signal for the specific portion of the cardiac cycle, and (c) calculating at least one time-varying parameter of the generated HF electrogram signal, wherein the specific portion of the cardiac cycle includes at least part of a specific segment of the cardiac cycle, the specific segment of the cardiac cycle being one of a group consisting of a P segment, a Q segment, a R segment, a S segment, a T segment, and a QRS complex segment.

According to some embodiments of the invention, at least 80% of the specific segment of the cardiac cycle is within the specific portion of the cardiac cycle.

According to some embodiments of the invention, the measuring the electrogram signal at a high frequency only during a specific segment of a cardiac cycle includes measuring an electrogram signal at any frequency only during a specific segment of a cardiac cycle.

According to some embodiments of the invention, further including the calculating includes calculating only when a correlation coefficient value of the generated HF electrogram signal to a template is larger than a threshold value.

According to some embodiments of the invention, further including the calculating includes calculating only when a noise level of the generated HF electrogram signal is smaller than a threshold value.

According to some embodiments of the invention, further including aligning a plurality of HF electrogram signals based on synchronization of the HF electrogram signals relative to a pacing signal.

According to some embodiments of the invention, further including aligning a plurality of HF electrogram signals to a predefined template. According to some embodiments of the invention, the predefined template is an electrogram segment from a prior heart beat. According to some embodiments of the invention, the predefined template is a curve calculated by averaging electrogram segments from a plurality of prior heartbeats. According to some embodiments of the invention, the predefined template is a curve calculated by fitting parameters to an inherent electrogram signal.

According to some embodiments of the invention, further including an electrogram segment in the averaging of the electrogram segments only when a noise level of the electrogram segment is smaller than a threshold value.

According to some embodiments of the invention, the providing at least one electrogram signal from an electrode located within a subject's body includes measuring an electrogram signal by using at least one electrode selected from a group consisting of (a) an intracardiac electrode, (b) a subcutaneous electrode, (c) a can of an implanted device, (d) a combination of two of the above.

According to some embodiments of the invention, the specific segment of the cardiac cycle is a P segment, and the analysis is used to provide warning of a condition selected from a group consisting of an irregular propagation of an action potential in a cardiac atria, atrial tachycardia, atrial bradycardia, and atrial arrhythmia.

According to some embodiments of the invention, the specific segment of the cardiac cycle is a P segment, and the analysis is used to provide warning of atrial arrhythmia, and further including manipulating a pacing rate to overcome the atrial arrhythmia.

According to some embodiments of the invention, the manipulating the pacing rate to overcome the atrial arrhythmia includes increasing the pacing rate and gradually decreasing the pacing rate.

According to some embodiments of the invention, the specific segment of the cardiac cycle includes a QRS complex, and the analysis is used to provide warning of onset of an ischemic event.

According to some embodiments of the invention, further including reducing a pacing rate.

According to some embodiments of the invention, the analysis includes detection of a reduction in amplitude of the HF electrogram signal.

According to some embodiments of the invention, the measuring the electrogram signal at a high frequency includes measuring only a sub band smaller than 500 Hz in a range of 100-2000 Hz.

According to some embodiments of the invention, the measuring only a sub band includes measuring in a sub band range where the sub band range is smaller than a highest frequency of the sub band divided by 2.

According to some embodiments of the invention, the measuring only a sub band includes measuring in a sub band range where the sub band range is smaller than twice a lowest frequency of the sub band.

According to some embodiments of the invention, the sampling of the electrogram signal at a high frequency includes sampling the electrogram signal at a high frequency during a specific segment of a breathing cycle.

According to some embodiments of the invention, further including aligning and averaging a plurality of HF electrogram signals in which the aligning includes synchronization of HF electrogram signals based on a pacing signal.

According to some embodiments of the invention, further including comparing a value of the time-varying parameter of the HF electrogram signal and a baseline value of the time-varying parameter of the HF electrogram signal.

According to some embodiments of the invention, further including comparing a value of the time-varying parameter of the HF electrogram signal and a prior value of the time-varying parameter of the HF electrogram signal under same heart rate conditions.

According to some embodiments of the invention, the same conditions are selected from a group consisting of (a) same heart rate, (b) same heart rate increase, (c) same heart rate decrease, (d) same pattern of change of heart rate.

According to some embodiments of the invention, further including comparing a current value of the time-varying parameter of the HF electrogram signal and a prior value of the of the time-varying parameter of the HF electrogram signal in which the prior value was measured for a heart rate different by a pre set amount from a heart rate at which the prior value was measured.

According to an aspect of some embodiments of the present invention there is provided an implantable device for analyzing a high frequency (HF) electrogram signal including an implantable electrode for use inside a living body, a signal pickup configured to pick up an electrogram signal including a high frequency (HF) component, a measurement unit for measuring a high frequency (HF) component of the electrogram signal only during a specific segment of a breathing cycle, and an analyzer for analyzing the HF component of the electrogram signal, wherein the signal pickup, the measurement unit and the analyzer are included within an implantable container, the analyzer is configured to analyze at least one time-varying parameter of the HF component of the electrogram signal, and the analyzer is configured to determine the specific segment of the breathing cycle.

According to an aspect of some embodiments of the present invention there is provided a method for analyzing a high frequency (HF) electrogram signal including (a) providing at least one electrogram signal from an electrode located within a subject's body, (b) measuring the electrogram signal at a high frequency only during a specific segment of a breathing cycle, generating a HF electrogram signal for the specific segment of the breathing cycle, and (c) having a computer measure at least one time-varying parameter of the HF electrogram signal.

According to some embodiments of the invention, HF ECG parameters are measured only once during a breathing cycle.

According to some embodiments of the invention, the specific segment of the breathing cycle is measured by at least one motion sensors in an implanted device.

According to an aspect of some embodiments of the present invention there is provided IPG (implantable pulse generator) apparatus for analyzing a high frequency (HF) electrogram signal including an electrode for use inside a living body, a signal pickup configured to pick up an electrogram signal including a high frequency (HF) component, a measurement unit for measuring a high frequency (HF) component from the electrogram signal during a specific segment of a cardiac cycle, and an analyzer for analyzing the HF component of the electrogram signal, wherein the signal pickup, the measurement unit and the analyzer are included within an implantable container, and the analyzer is configured to measure at least one time-varying parameter of the HF electrogram signal and to detect a change in the time-varying parameter in comparison to a baseline value of the time-varying parameter.

According to some embodiments of the invention, the analyzer is adapted to receive a synchronization signal from a pacing unit in the apparatus.

According to some embodiments of the invention, the analyzer is adapted to receive a synchronization signal from a pacing unit in the apparatus and a detection of the specific segment of the cardiac cycle is based, at least in part, on the synchronization signal from the pacing unit.

According to some embodiments of the invention, the electrode includes a bipolar electrode. According to some embodiments of the invention, the electrode includes a monopolar electrode.

According to an aspect of some embodiments of the present invention there is provided a method for analyzing a high frequency (HF) electrogram signal including (a) providing a first electrogram signal from a first location of an intracoronary electrode adjacent to an occlusion of a coronary artery and proximal to the occlusion, (b) sampling the first electrogram signal at a high frequency, generating a first high frequency (HF) electrogram signal, (c) providing a second electrogram signal from a second location of an intracoronary electrode adjacent to the occlusion of the coronary artery and distal to the occlusion, (d) sampling the second electrogram signal at a high frequency, generating a second high frequency (HF) electrogram signal, (e) measuring at least one time varying parameter of the first HF electrogram signal and at least one time varying parameter of the second HF electrogram signal, and (f) comparing, by a computer, the at least one time varying parameter of the first HF electrogram signal and the at least one time varying parameter of the second HF electrogram signal and produce a result of the comparison.

According to some embodiments of the invention, the intracoronary electrode includes a monopolar electrode. According to some embodiments of the invention, the intracoronary electrode includes a bipolar electrode.

According to some embodiments of the invention, the occlusion of the coronary artery is a suspected occlusion of the coronary artery.

According to some embodiments of the invention, the at least one parameter of the first HF electrogram signal and the second HF electrogram signal includes an RMS value of the electrogram signals, and the comparison includes a difference between the RMS values at the first location and the second location.

According to some embodiments of the invention, the comparison includes a function of numerical characteristics of an envelope of the first HF electrogram signal and an envelope of the second HF electrogram signal.

According to some embodiments of the invention, the comparison includes a detection of a difference in ischemic condition between a first HF index and a second HF index.

According to some embodiments of the invention, further including analyzing results from fractional flow reserve measurement (FFR).

According to some embodiments of the invention, further including determining whether stent therapy is needed based on the result of the comparison.

According to some embodiments of the invention, further including post-revascularization assessment of revascularization based on the result of the comparison.

According to some embodiments of the invention, further including assessment of a current ischemic condition based on the result of the comparison.

According to an aspect of some embodiments of the present invention there is provided apparatus for analyzing a high frequency (HF) electrogram signal including an electrode for use inside a living body, a signal pickup configured to pick up an electrogram signal including a high frequency (HF) component, a measurement unit for measuring a high frequency (HF) component from the electrogram signal during a specific segment of a cardiac cycle, and an analyzer for analyzing the HF component of the electrogram signal, wherein the analyzer is configured to compare at least one time-varying parameter of the HF electrogram signal measured at a first location within a subject's body and at least one time-varying parameter of the HF electrogram signal measured at a second location within a subject's body, and to produce a result of the comparison.

According to some embodiments of the invention, further including a setting for determining whether stent therapy is needed based on the result of the comparison.

According to some embodiments of the invention, further including a setting for post-revascularization assessment of revascularization based on the result of the comparison.

According to some embodiments of the invention, further including a setting for assessment of a current ischemic condition based on the result of the comparison.

According to an aspect of some embodiments of the present invention there is provided a method for analyzing a high frequency (HF) electrogram signal including (a) providing at least one electrogram signal between a first electrode at a first location within a subject's body and a second electrode at a second location within a subject's body, the first location and the second location being adjacent to a heart, opening at least a 90 degree angle relative to a direction toward a center of mass of the heart, (b) measuring the electrogram signal at a high frequency generating a HF electrogram signal, (c) having a computer measure at least one time-varying parameter of the HF electrogram signal, (d) having a computer detect a change in the time-varying parameter in comparison to a baseline value of the time-varying parameter, and (e) having the computer generate an alert based, at least in part, on the detection.

According to an aspect of some embodiments of the present invention there is provided an implantable device for analyzing a high frequency (HF) electrogram signal received from subcutaneous, above-rib pickup locations, the device including an implantable electrode for use inside a living body, and a can for subcutaneous implantation, the can including a signal pickup configured to pick up an electrogram signal including a high frequency (HF) component, a signal filter connected to the signal pickup and configured to measure a high frequency (HF) component from the electrogram signal, and an analyzer for analyzing the HF component of the electrogram signal, wherein the analyzer is configured to analyze at least one time-varying parameter of the HF component of the electrogram signal, and the signal filter is configured to measure the electrogram signal by using a signal picked up from at least two pickup locations which are both subcutaneous and above-rib.

According to some embodiments of the invention, the two pickup locations include a subcutaneous, above-rib electrode pickup location and a can pickup location.

According to some embodiments of the invention, the signal pickup is also configured to pick up a low frequency component, the signal filter is also configured to measure the low frequency component from the electrogram signal, and the analyzer is also configured to analyze the low frequency component of the electrogram signal.

According to some embodiments of the invention, the analyzer is configured to analyze three voltage potential difference signals simultaneously, the three voltage potential difference signals including voltage potential difference signals between the can and a first subcutaneous pickup location, the can and a second subcutaneous pickup location, and the first subcutaneous pickup location and the second subcutaneous pickup location.

According to some embodiments of the invention, the analyzer is configured to analyze the HF component of the electrogram signal and the low frequency component of the electrogram signal simultaneously.

According to an aspect of some embodiments of the present invention there is provided a method for analyzing a high frequency (HF) electrogram signal including receiving an electrogram signal from at least two subcutaneous, above-rib pickup locations at a can for subcutaneous, above-rib implantation, the can including a signal pickup configured to pick up an electrogram signal including a high frequency (HF) component, a signal filter connected to the signal pickup and configured to measure a high frequency (HF) component from the electrogram signal, and an analyzer for analyzing the HF component of the electrogram signal, wherein the analyzer is configured to analyze at least one time-varying parameter of the HF component of the electrogram signal, and the signal filter is configured to measure the electrogram signal by using a signal picked up from at least two pickup locations, picking up an electrogram signal, and analyzing the HF component of the electrogram signal.

According to some embodiments of the invention, the at least two subcutaneous, above-rib pickup locations include two subcutaneous, above-rib, pickup locations selected from a group consisting of two electrodes at mid-chest pickup locations, two electrodes at right-of-sternum pickup locations, and two electrodes at left-of-sternum pickup locations.

According to some embodiments of the invention, the two pickup locations include a subcutaneous, above-rib electrode pickup location and a subcutaneous, above-rib can pickup location.

According to some embodiments of the invention, the signal pickup is also configured to pick up a low frequency component, the signal filter is also configured to measure the low frequency component from the electrogram signal, and the analyzer is also configured to analyze the low frequency component of the electrogram signal.

According to some embodiments of the invention, the analyzer is configured to analyze three voltage potential difference signals simultaneously, and the three voltage potential difference signals include voltage potential difference signals between the can and a first subcutaneous pickup location, the can and a second subcutaneous pickup location, and the first subcutaneous pickup location and the second subcutaneous pickup location.

According to some embodiments of the invention, the analyzer analyzes the HF component of the electrogram signal and the low frequency component of the electrogram signal simultaneously.

According to an aspect of some embodiments of the present invention there is provided a method for analyzing a high frequency (HF) electrogram signal including: (a) providing at least one electrogram signal from a first electrogram signal pickup located adjacent to and upstream of a narrowing of a subject's blood vessel, (b) providing at least one electrogram signal from a second electrogram signal pickup located adjacent to and downstream of the narrowing of the blood vessel, (c) measuring a HF component of the electrogram signals from the upstream and the downstream locations, and (d) analyzing at least one time-varying parameter of the HF electrogram signals.

According to some embodiments of the invention, the first electrogram signal pickup and the second electrogram signal pickup are included in one electrode.

According to some embodiments of the invention, the first electrogram signal pickup and the second electrogram signal pickup are included in separate electrodes.

According to some embodiments of the invention, at least one of the electrogram signal pickups includes bipolar pickup.

According to some embodiments of the invention, the first electrogram signal pickup and the second electrogram signal pickup are electrically connected to an electronics unit which communicates wirelessly with an external analyzer, transmitting a signal based on an HF signal picked up by the electrogram signal pickups.

According to some embodiments of the invention, the electrogram signal from the first electrogram signal pickup and the electrogram signal from the second electrogram signal pickup are measured by a same electrogram signal pickup located upstream of the narrowing of the blood vessel and downstream of the narrowing of the blood vessel at different times.

According to some embodiments of the invention, further including FFR (fractional flow reserve) analysis.

According to some embodiments of the invention, further including determining whether stent placement is recommended based, at least in part, on the analyzing at least one time-varying parameter of the HF electrogram signals and on the FFR (fractional flow reserve) analysis.

According to some embodiments of the invention, further including determining post-revascularization efficacy of the revascularization based, at least in part, on the analyzing at least one time-varying parameter of the HF electrogram signals and on the FFR (fractional flow reserve) analysis.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
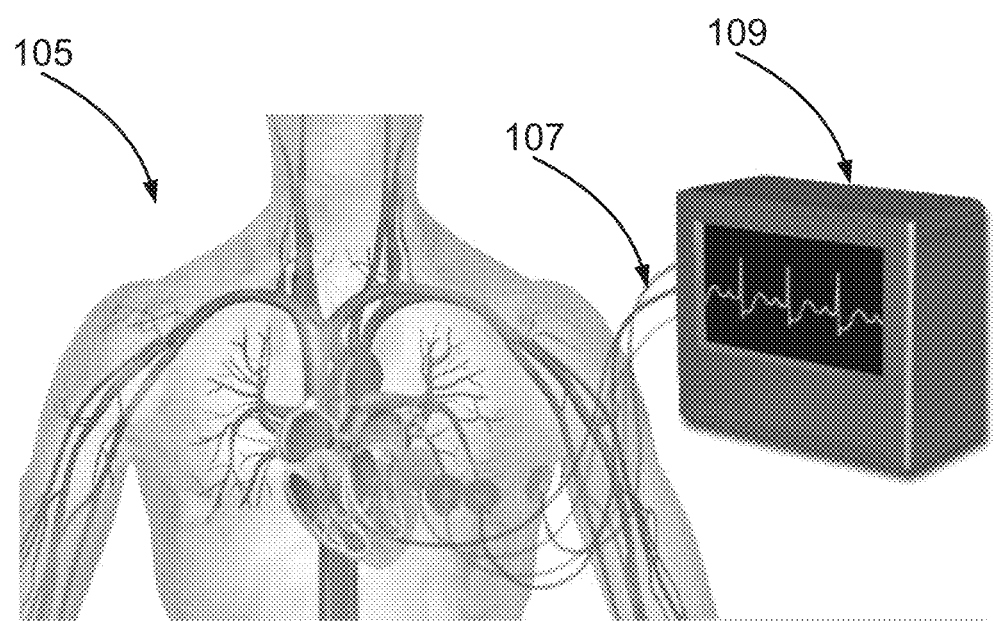
FIG. 1A is a simplified illustration of a prior art apparatus for detecting myocardial ischemia using analysis of high frequency components of an electrocardiogram.

The present invention, in some embodiments thereof, relates to an apparatus and method for detecting myocardial ischemia using analysis of high frequency components of an electrocardiogram and/or of a cardiac electrogram, and, more particularly, but not exclusively, to an implantable such apparatus and method.

A broad aspect of some embodiments of the invention relates to measuring a HF (high frequency) electrogram from inside the body, for example, using electrodes which are also used for IPGs (implantable pulse generators), for example, for a pacemaker, a cardiac resynchronization therapy (CRT) and/or a defibrillator or cardioverter, or other implantable devices with signal sensing capabilities like neurostimulators or implantable electrogram recorders.

An aspect of some embodiments of the invention relates using a significant amount of collected data to reduce noise and/or increase sensitivity of HF electrogram measurements. In typical, out of body HF electrocardiogram measurements, the signal is often noisy and it is difficult to measure long periods while the heart is stressed (e.g., in a stress test). In an exemplary embodiment of the invention, use is made of an implantable measurement device to provide a high quality intracardiac electrogram signal, providing a significant amount of data, potentially over a period of hours, days, weeks, months, even years. The signal is collected on a routine basis and HF electrogram values are measured for recording of long term values that sometimes serve as a baseline for clinical diagnosis and long term status of the subject and short term values that provide an indication on a current transient status. In an exemplary embodiment of the invention, the data is used to provide a reliable baseline. Optionally or alternatively, the data is used to provide a baseline for multiple categories, for example, different baselines for different values of physiologically related and/or measured parameters (e.g., one or more of movement, blood pressure, time of day, ischemia, eating, sleeping), ECG morphologies, breathing cycle portions and/or types, pacing activity and/or parameters, heart rate. Optionally or alternatively, the data is used to analyze simultaneously two or more HF electrogram parameters, such as amplitude and morphology, potentially providing a more robust analysis of the subject's condition.

In some embodiments, a result of the analysis of the electrogram signal is optionally stored. In some embodiments, the analysis and/or the storing include compression of the result of the analysis.

An aspect of some embodiments of the invention relates to changing behavior of an IPG based on results of the analysis. In some embodiments, the IPG changes pulse generation timing based on the results of the analysis. In some embodiments, a CRT changes output based on the results of the analysis.

An aspect of some embodiments of the invention relates to synchronizing the acquisition and/or analysis of HF electrogram signals to a breathing parameter. In an exemplary embodiment of the invention, it is noted that the breathing cycle has an effect on the autonomous nervous system and on various actions and reactions of the heart. In an exemplary embodiment of the invention, measurement comprises binning measurements according to a breath cycle.

An aspect of some embodiments of the invention relates to synchronizing data acquisition and/or analysis activities to particular parts of the cardiac cycle and/or local electrical activity. Optionally, an acquisition window is defined, for example, based on an estimated time when a signal of interest is expected (e.g., based on a pacing signal or an analysis of a previous signal) and/or based on a trigger signal (e.g., a local sensing of electrical activity at the measurement location or remote therefrom). In an exemplary embodiment of the invention, only data acquired in the window is analyzed and/or acquired at high frequency.

In some embodiments, the acquisition window is optionally opened based on an estimated time following reception of a pacing signal.

In some embodiments, the acquisition window is optionally opened based on detecting a specific point in a low-frequency electrogram signal, such as, by way of a non-limiting example, a beginning of a QRS complex, or a P segment, or a Q segment, or a R segment, or a S segment, or a T segment.

In some embodiments, the acquisition window is optionally opened based on a signal indicating a specific physiological condition, such as a specific portion of a breathing cycle, as described in more detail below with reference to FIG. 3.

In some embodiments, the acquisition window is closed based on detecting a specific point in a low-frequency electrogram signal, such as, by way of a non-limiting example, an end of a QRS complex, or a P segment, or a Q segment, or a R segment, or a S segment, or a T segment.

In an exemplary embodiment of the invention, the measured HF electrogram signal is not of an entire QRS complex, rather the measurement reflects a segment of the QRS complex. In some cases this segment relates to the location of the implantable electrode location.

In an exemplary embodiment of the invention, the portion of the cardiac cycle which is acquired and/or analyzed is less than 50%, 30%, 20%, 10%, 5% or intermediate percentages of the time.

In an exemplary embodiment of the invention, selective data acquisition is applied in conjunction with such synchronizing, for example, acquiring and/or analyzing HF electrogram signals only if both timing and one or more other criteria are met. For example, acquisition may depend on both breathing cycle and time in cardiac cycle. For example, acquisition may be performed during similar physiological conditions such as similar pulse rate, during a subject's sleep, etc. by way of a non-limiting example, sleeping is optionally detected by measuring heart rate and/or heart rate variability.

An aspect of some embodiments of the invention relates to measuring local HF electrogram signals, for example, between two electrodes that are at or near the heart, rather than between an electrode in the heart and an electrode far from the heart. In an exemplary embodiment of the invention, this allows an HF electrogram signal to be mostly of a small part of the heart (e.g., less than 50%, 40%, 30%, 20%, 10% or intermediate percentages of a muscle mass volume thereof). In an exemplary embodiment of the invention, the measurement is using bipolar electrodes (or other multiple electrodes on a same lead) which measure HF electrogram contributions from nearby tissue, for example, to within a distance of less than 5 cm, 3 cm, 2 cm, 1 cm or intermediate distances. Optionally or alternatively, the measurement is using separate electrodes, for example, one atrial electrode and one ventricular electrode, and the measured tissue lies between the pair of electrodes. In some embodiments more than two electrodes are used. In some embodiments two or more electrodes are used and their signals optionally combined, optionally averaging the signals provided by both.

In some embodiments, the HF electrogram is optionally picked up and/or measured and/or analyzed excluding times when a pacing signal is provided by a pacing unit.

In an exemplary embodiment of the invention, at least one electrode is placed so that a significant part of the heart can be assessed, for example, at least 30%, 50%, 60% or intermediate parts of the heart. Optionally, such measurement is between an intra-cardiac electrode or an electrode adjacent the heart and the can of an IPG or a remote electrode or an electrode at another side of the heart. It is noted that measuring a signal between electrodes placed at different locations potentially enables measuring the difference in tissue between a source of an electric signal (natural or artificial pacing) and the electrode location.

An aspect of some embodiments of the invention relates to identifying local ischemia by comparing a first measurement and a second measurement which are separated in time and/or space. In some embodiments, a value of a function of several measurements which are separated in time and/or space may be computed in order to compare values of the function and/or to derive a clinical indicator.

By way of a non-limiting example, calculating a base line value at a specific time when it is clear that a patient is not showing sign of ischemia. Such measurement and/or calculation may optionally be done during a physician check up, and/or during a specific time of the day, and/or during low heartrate (HR) value, for example a lowest HR value every day, and/or during sleep, optionally during a deep sleep stage. In some embodiments a baseline is optionally measured during a period with a highest HR variability during a day. In some embodiments the baseline value is optionally compared to a measured value at a different time. In some embodiments the different time is optionally a selected timing such as a time with a specific heartrate, and/or during exercise activity, and/or during REM sleep, and/or during a time with minimal heart rate variability during the day In an exemplary embodiment of the invention, the criticality of a stenosis or other vascular flow abnormality is determined by measuring HF electrogram components upstream and downstream (or within) the abnormality. It is expected that significant (e.g., should be treated) abnormalities will show a significant difference in ischemia between the upstream and downstream locations. A non-limiting example difference may optionally be a change in HF RMS values greater than 2%, 5%, 10% or 20%, 30%, 40% or 50%.

In another example, ischemia levels at difference localities are measured using pairs of electrodes as described above. Optionally, this comparison is used to assess progress of treatment and/or disease and/or to determine changes in ischemia in different parts of the heart as a function of condition (e.g., physiological state, stress, sleep).

In an exemplary embodiment of the invention, the comparison is over time, by comparing the degree of ischemia under different conditions.

In an exemplary embodiment of the invention, electrode placement is selected to ensure the ability to measure desired localities and/or compare such localities.

An aspect of some embodiments of the invention relates to electrogram signals gathered from implanted electrodes being stronger than electrocardiogram signals gathered from electrodes attached to a subject's skin.

In some embodiments, the implanted electrodes are optionally connected, directly or wirelessly, to an analyzer external to a subject's body. In some embodiments, the implanted electrodes are optionally connected to an analyzer also implanted in the subject's body. In some embodiments, at least one electrode, or at least a reference potential, is measured at the implanted analyzer body, also termed a can.

In some embodiments, the implanted electrodes are optionally connected to an IPG, optionally a pacemaker with processing capabilities, and the analyzer is included in the IPG can. In some embodiments the analyzer includes adding components to a pacemaker, in some embodiments the analyzer includes software which runs on a pacemaker processor.

In some embodiments, the same electrodes used for measuring the electrogram or for providing a pacing signal by the pacemaker, CRT, ICD or any other implantable device are optionally used to pick up the electrogram.

In some embodiments, the electrogram signal is not picked up while a pacing signal is provided by the pacemaker. Since the pacing signal is short, typically on the order of one millisecond, once per heartbeat, the same electrodes used for pacing can optionally be used to pick up the electrogram during the rest of the time.

In some embodiments, the electrogram signal is not picked up for 5, 10, 15, 20, 25, 30 or even 50 milliseconds following a pacing signal by the pacemaker.

In some embodiments, a QRS complex signal triggered by pacing is not picked up. In some embodiment, the smart pacemaker provides a signal to an electrogram pickup unit, and the electrogram pickup unit is thus notified when a QRS complex signal is triggered by pacing.

Modern pacemakers do not provide pacing signals all the time, only responsive to a subject's heart rate and/or heart condition. In such pacemakers the same electrodes used for pacing are optionally used to pick up the electrogram, since the electrodes are not being used to provide pacing signals during most of the time.

An aspect of some embodiments of the invention relates to the stronger electrogram signals being synergistically conducive to analyzing high frequency (HF) electrocardiogram signals, which are weak when gathered from electrodes attached to a subject's skin. Potentially, various known techniques such as described in the references listed in the Background section, are able to be carried out with less interfering noise, potentially at higher quality, potentially at higher signal to noise ratio (SNR), potentially over shorter measurement durations.

An aspect of some embodiments of the invention relates to alignment of the electrogram signals.

In some embodiments alignment of electrogram signals from different heart beats is optionally performed by correlation of low frequency components of the electrogram signals, and/or by correlation of high frequency components of the electrogram signals, and/or by synchronizing relative to a pacemaker pulse, and/or by synchronizing relative to detected atrial depolarization by using an atrial electrode. In some embodiments the alignment is of an electrogram signal to an inherent electrogram signal, as will be described further below.

An aspect of some embodiments of the invention relates to saving power in an implanted device by gathering electrogram signals only during a specific fraction of time, potentially lengthening duration of operation between possible battery charging and/or battery replacing.

An aspect of some embodiments of the invention relates to saving power in an implanted device by gathering electrogram signals only during a specific fraction of the cardiac cycle.

An aspect of some embodiments of the invention relates to saving power in an implanted device by gathering electrogram signals only during a specific fraction of the QRS complex segment of the cardiac cycle.

An aspect of some embodiments of the invention relates to saving power in an implanted device by gathering electrogram signals only during a specific fraction of a breathing cycle, potentially comparing like signals to like signals, since some features of an electrogram signal typically correlate to the breathing cycle, and potentially lengthening duration of operation between possible battery charging.

An aspect of some embodiments of the invention relates to measuring the HF electrogram when the heart rate is within a specific range of heart rates.

An aspect of some embodiments of the invention relates to electrogram signals gathered from implanted electrodes enabling placing the electrodes at locations physiologically different than only electrodes attached to a subject's skin.

An aspect of some embodiments of the invention relates to analyzing high frequency (HF) electrogram signals which are picked up proximally and distally to an occlusion in a blood vessel. Comparing the above-mentioned signals potentially indicates a change in tissue before and after the occlusion, and/or a degree of the occlusion. In some embodiments, the comparison of the HF electrogram signals may optionally be performed in a same procedure as performing a fractional flow reserve (FFR) measurement, and results of both measurements may be combined to indicate degree of the occlusion and/or suggest a method of treatment of the occlusion.

For purposes of better understanding some embodiments of the present invention, reference is first made to FIG. 1A, which is a simplified illustration of a prior art apparatus for detecting myocardial ischemia using analysis of high frequency components of an electrocardiogram.

FIG. 1A depicts a thorax 105, with electrodes 107 attached to the thorax 105 and to a device 109 for analysis of high frequency components of an electrocardiogram.

Figure 1B:
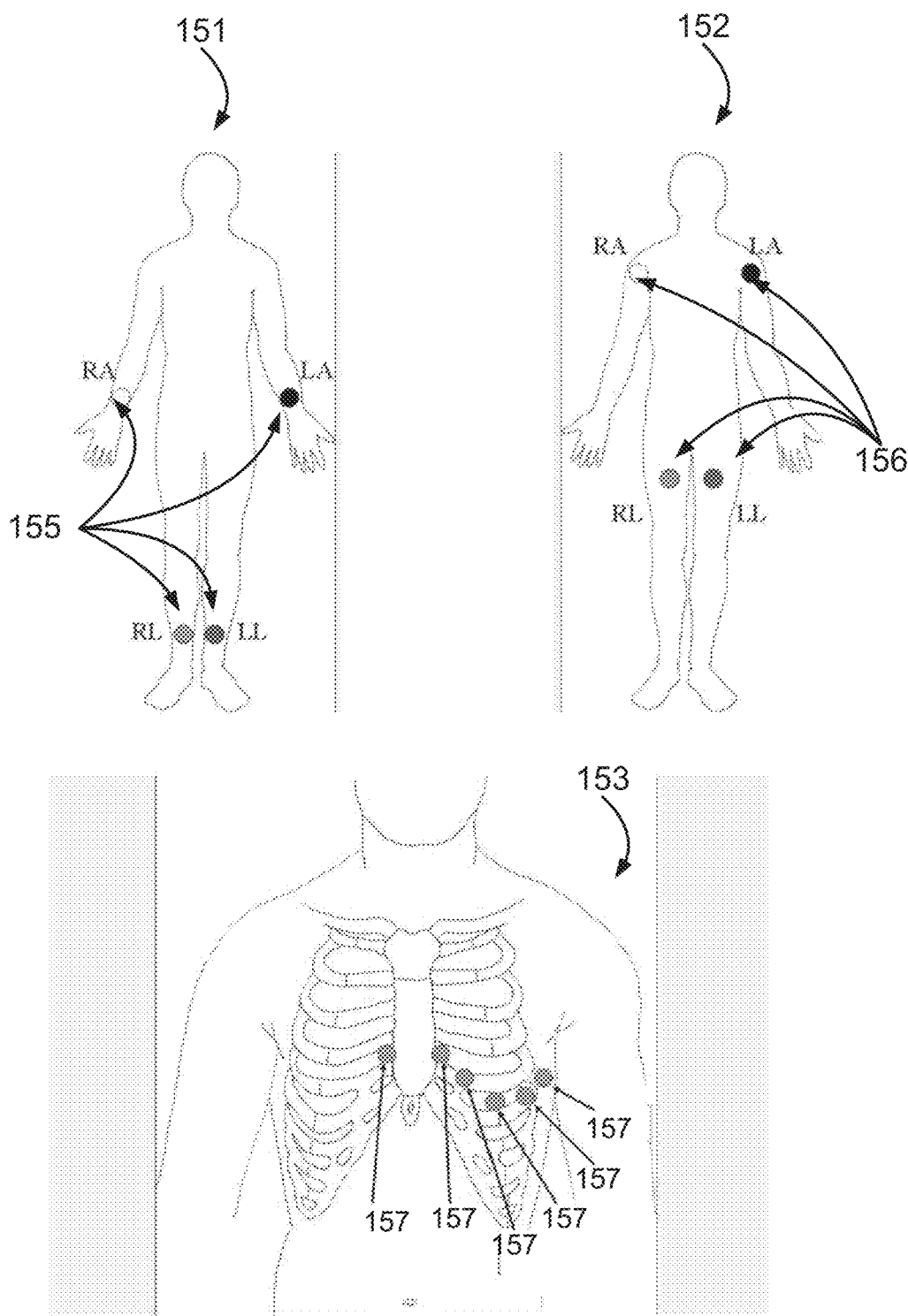
FIG. 1B is a simplified illustration of typical prior art locations for attaching pickup electrodes, including electrodes for picking up high frequency components of an electrocardiogram.

Reference is also made to FIG. 1B, which is a simplified illustration of typical prior art locations for attaching pickup electrodes, including electrodes for picking up high frequency components of an electrocardiogram.

FIG. 1B depicts three line FIGS. 151 152 153 of human subjects, and three sets of locations 155 156 157 for placing electrodes for picking up high frequency components of an electrocardiogram.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1C:
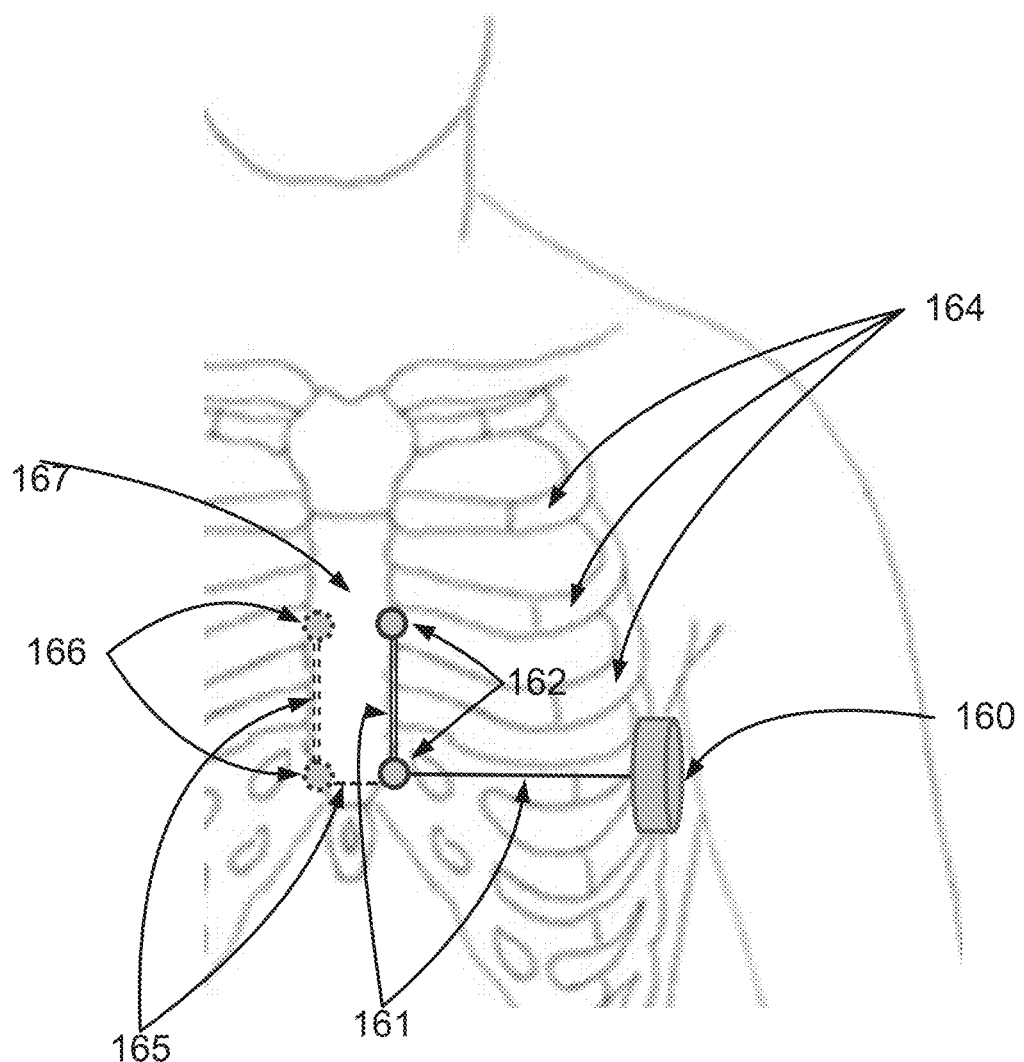
FIG. 1C is a simplified illustration of a subcutaneous apparatus for analyzing an electrogram according to an example embodiment of the invention.

Reference is now made to FIG. 1C, which is a simplified illustration of a subcutaneous apparatus for analyzing an electrogram according to an example embodiment of the invention.

FIG. 1C depicts a simplified illustration of a subcutaneously implanted electronics box, also termed a can 160, and with one or more electrode wires 161 165 optionally electrically connecting the can 160 with one or more electrodes at one or more subcutaneous electrogram signal pickup locations 162 166.

FIG. 1C depicts a can 160 implanted under skin (not shown) and above ribs 164.

In some embodiments, the can 160 is electrically connected by the electrode wires 161 to example electrodes at subcutaneous pickup locations 162 depicted in FIG. 1C, which are optionally over the ribs 164, under the skin (not shown) and on a left edge of a subject's sternum 167.

In some embodiments, the can 160 is electrically connected by electrode wires 165 to electrodes at example pickup locations 166 depicted in FIG. 1C, which are optionally over the ribs 164, under the skin (not shown) and on a right edge of the subject's sternum 167.

It is noted that implanted pickup locations 162 166, even external to the ribs 164, potentially benefit from a signal which contains significantly less noise than a pickup location on the skin surface.

In some embodiments, an electrogram signal corresponds to a voltage potential difference between two pickup locations connected by one or more electrode wires to the can 160.

In some embodiments, an electrogram signal corresponds to a voltage potential difference between a subcutaneous pickup location external to the can 160, and a pickup location at the can 160.

In some embodiments the can 160 is optionally placed at a ventral position on a subject (not shown).

In some embodiments the can 160 is optionally placed at a dorsal position on a left side of the body, as depicted in FIG. 1C.

In some embodiments the can 160 is optionally placed at a subcutaneous position at a left top of a chest.

In some embodiments the can 160 is optionally placed at a subcutaneous position on a subject's back.

Figure 2A:
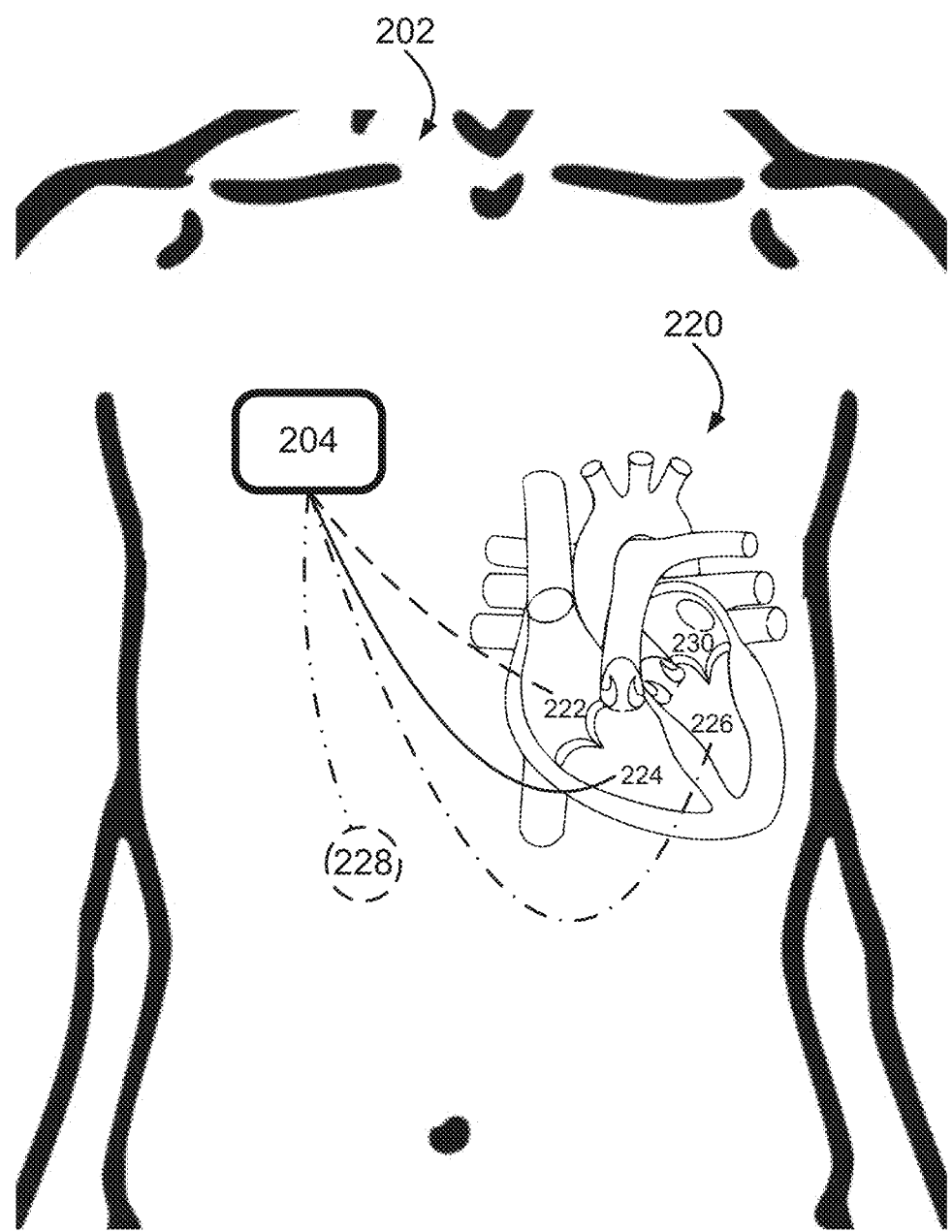
FIG. 2A is a simplified illustration of apparatus for analyzing an electrogram according to an example embodiment of the invention.

Reference is now made to FIG. 2A, which is a simplified illustration of apparatus for analyzing an electrogram according to an example embodiment of the invention.

FIG. 2A shows a schematic depiction of a chest 202, with an implanted electronics box, also termed an implantable device 204 also termed a can, and with one or more electrodes electrically connecting the device 204 with one or more electrogram signal pickup locations. Example pickup locations depicted in FIG. 2A include the right atrium 222, the right ventricle 224, the left atrium 230, and the left ventricle 226. The electrogram signal pickup locations may optionally be located on a surface of the heart at epicardial locations. The electrogram signal pickup locations may optionally also be located in coronary veins and arteries such as the coronary sinus. The electrogram signal pickup locations may also be at some other place in a subject's thorax 228. FIG. 2A also depicts a schematic drawing of a heart 220.

The example embodiment of FIG. 2A depicts a first electrode location optionally located at the right atrium 222; a second electrode location optionally located at the right ventricle 224; a third electrode location optionally located at the left ventricle 226; and a fourth electrode location optionally located elsewhere in the thorax 228. The left atrium 230 of the heart is shown without an electrode in the present example embodiment.

It is noted that the device 204 is depicted as a schematic block, not necessarily depicted at the best location for the implantation.

In some embodiments the device 204 can is at least partially conductive and may optionally serve as an additional electrogram signal pickup location.

It is noted that some embodiments may optionally include an electrode located at the left atrium 230. In some embodiments there may optionally be an electrode located at the left atrium 230 for use in pacing, optionally without using the electrode for electrogram pickup.

Example Electrode Locations

In some example embodiments the electrogram signal is measured between two electrodes which are placed both in the same heart chamber.

In some example embodiments the electrogram signal is measured between an electrode which is placed in a heart chamber and an electrode which is placed outside the heart chamber.

In some example embodiments the electrogram signal is measured between an electrode which is placed in a first heart chamber and an electrode which is placed in a second heart chamber.

In some example embodiments the electrogram signal is measured between an electrode which is placed touching a heart an electrode which is electrically coupled to a device can.

In some example embodiments the electrogram signal is optionally measured between two locations adjacent to a heart, the two locations having at least 50% of the mass of the heart between them.

In some example embodiments the electrogram signal is measured between an intracardiac electrode and an epicardiac electrode.

Figure 2B:
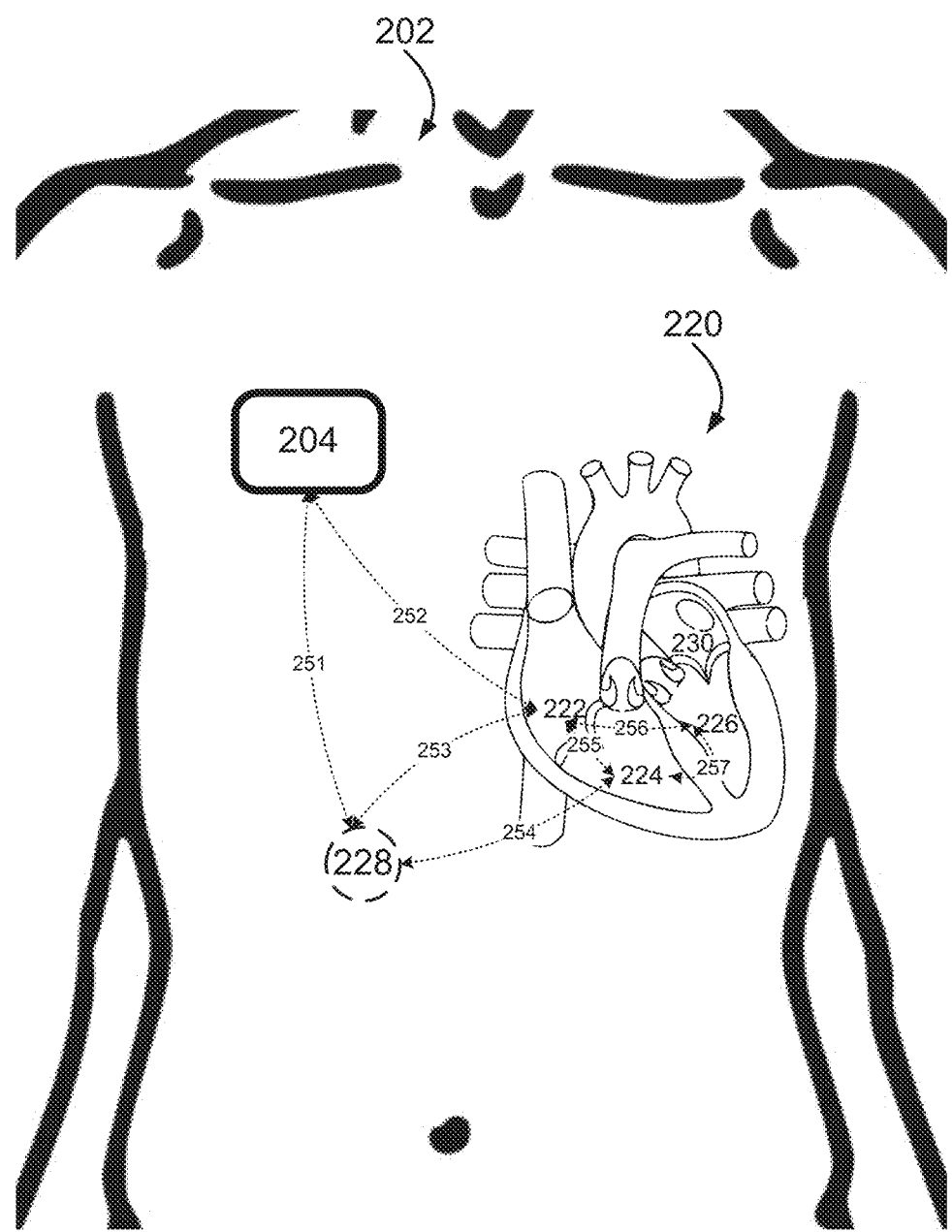
FIG. 2B is a simplified illustration of some non-limiting example potential differences measured by the example embodiment of FIG. 2A.

Reference is now additionally made to FIG. 2B, which is a simplified illustration of some non-limiting example potential differences measured by the example embodiment of FIG. 2A.

FIG. 2B depicts the schematic depiction of the chest 202, the device 204, the electrogram signal pickup locations 222 224 226 228 230, and the schematic depiction of the heart 220, as also shown in FIG. 2A.

FIG. 2B demonstrates some non-limiting examples of potential differences 251-257 measured between the electrogram signal pickup locations 204 222 224 226 228. The examples of potential differences 251-257 are a partial example of pairing of the locations 204 222 224 226 228 230.

In some examples, where bipolar electrodes are used, an electrogram signal may also optionally be measured between two poles on the same general location 204 222 224 226 228 230.

In some embodiments the system optionally performs simultaneous measurement of several electrogram signals from several pairs of electrodes, providing measurement of several electrogram vectors and/or indexes.

Figure 2C:
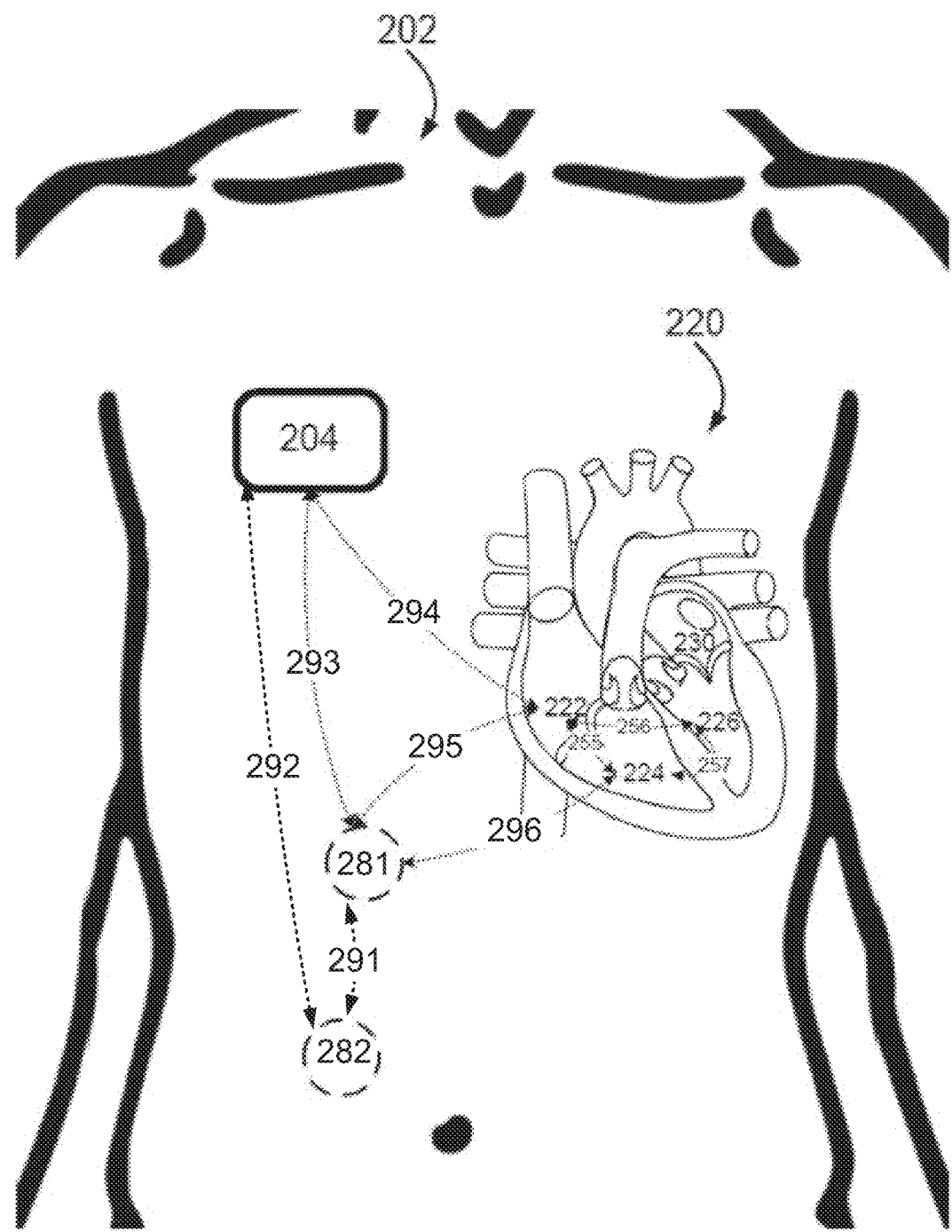
FIG. 2C is a simplified illustration of apparatus for analyzing an electrogram and some non-limiting example potential differences, according to an example embodiment of the invention.

Reference is now additionally made to FIG. 2C, which is a simplified illustration of apparatus for analyzing an electrogram and some non-limiting example potential differences, according to an example embodiment of the invention.

FIG. 2C demonstrates use of subcutaneous thoracic and/or abdominal electrodes and optionally use of a device "can", as an electrode.

FIG. 2C depicts the schematic depiction of the chest 202, the device 204, the electrogram signal pickup locations 204 222 224 226 230 281 282, and the schematic depiction of the heart 220.

FIG. 2C demonstrates some non-limiting examples of potential differences 291-296 and 255-257 measured between electrogram signal pickup locations 204 222 224 226 230 281 282. The examples of potential differences 291-296 and 255-257 are a partial example of pairing of the locations 204 222 224 226 230 281 282.

FIG. 2C specifically demonstrates locations 281 and 282 which are examples of subcutaneous thoracic and/or abdominal electrodes. In some embodiments the system may include 1, 2 or more thoracic and/or abdominal electrodes. In some embodiments, the device "can", depicted by reference number 204, is optionally also placed subcutaneously and optionally serves as an electrode.

It is noted that electrical potential differences are optionally measured between a pair of thoracic and/or abdominal electrodes, such as the potential difference 291, and/or between a thoracic and/or abdominal electrode and the device "can", such as the potential differences 292 293, and/or between a subcutaneous "can" and an intra-cardiac electrode, such as the potential difference 294, and/or between a thoracic and/or abdominal electrode and an intra-cardiac electrode, such as the potential differences 295 296.

In some examples, where bipolar electrodes are used, an electrogram signal may also optionally be measured between two poles on the same general location 204 222 224 226 230 281 282.

In some embodiments the system optionally performs simultaneous measurement of several electrogram signals from several pairs of electrodes, providing measurement of several electrogram vectors and/or indexes.

Figure 2D:
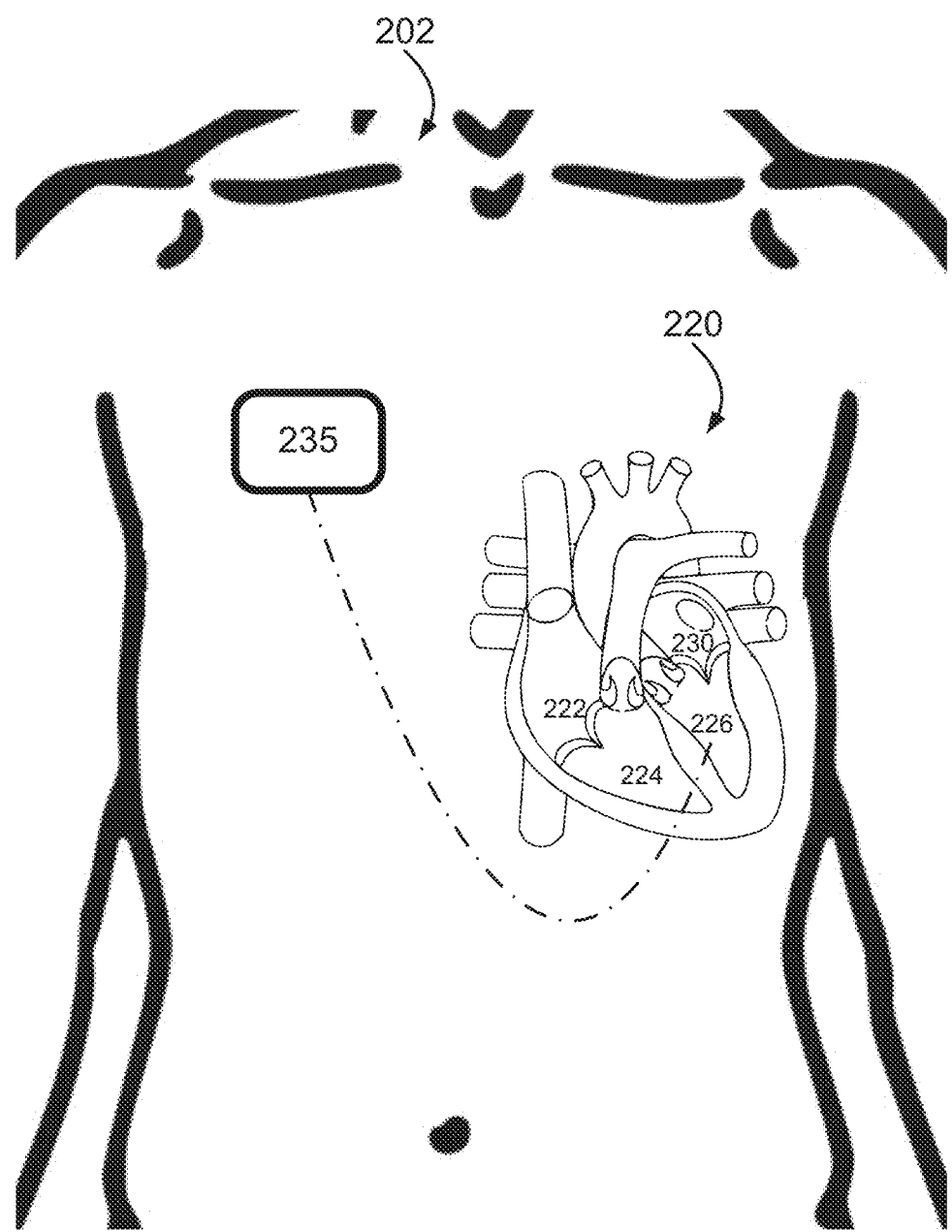
FIG. 2D is a simplified illustration of apparatus for analyzing an electrogram according to an example embodiment of the invention.

Reference is now additionally made to FIG. 2D, which is a simplified illustration of apparatus for analyzing an electrogram according to an example embodiment of the invention.

FIG. 2D shows a schematic depiction of a chest 202, with an implantable device 235, also termed a can, and with one monopole electrode electrically connecting the device 235 with an electrogram signal pickup location 226, optionally in the coronary sinus at a location in proximity to the left ventricle. FIG. 2D also depicts a schematic depiction of the heart 220. The electrode location may optionally be on a surface of the heart 220, optionally using an epicardial electrode, optionally attached and/or sutured to the surface of the heart 220.

It is noted that there are optionally many alternative configurations of measuring potential differences for producing an electrogram. The configurations include, by way of some non-limiting examples:

a monopole electrode and the can;

a bipolar electrode at each one of several heart locations (for example as shown in FIGS. 2A-2C);

between any 2 electrode positions in the heart, e.g. intracardiac, epicardiac (on the heart), in coronary blood vessels. By way of a non-limiting example—between the right atrium and the left ventricle;

between an electrode in the heart and an electrode in the thorax (for example as shown in FIGS. 2A-2C);

between two locations in the thorax (not shown); and between locations some of which are positioned at a cardiac blood vessel.

In some embodiments a bipolar electrode may optionally serve to measure a potential difference between two poles of the bipolar electrode.

In some embodiments a monopolar electrode may optionally serve to measure a potential difference between the monopolar electrode and the device can, and/or relative to a different electrode, whether the different electrode is another monopolar electrode or a bipolar electrode.

In various embodiments electrogram vectors are optionally produced from the potential differences measured. In various embodiments HF indexes, for example such as described in U.S. Pat. No. 8,626,275, are optionally calculated for some or all of the electrogram vectors.

In some embodiments at least the following HF indexes are optionally used: an RMS of the HF electrogram; an amplitude of the HF electrogram; and a morphology of the HF electrogram.

Figure 2E:
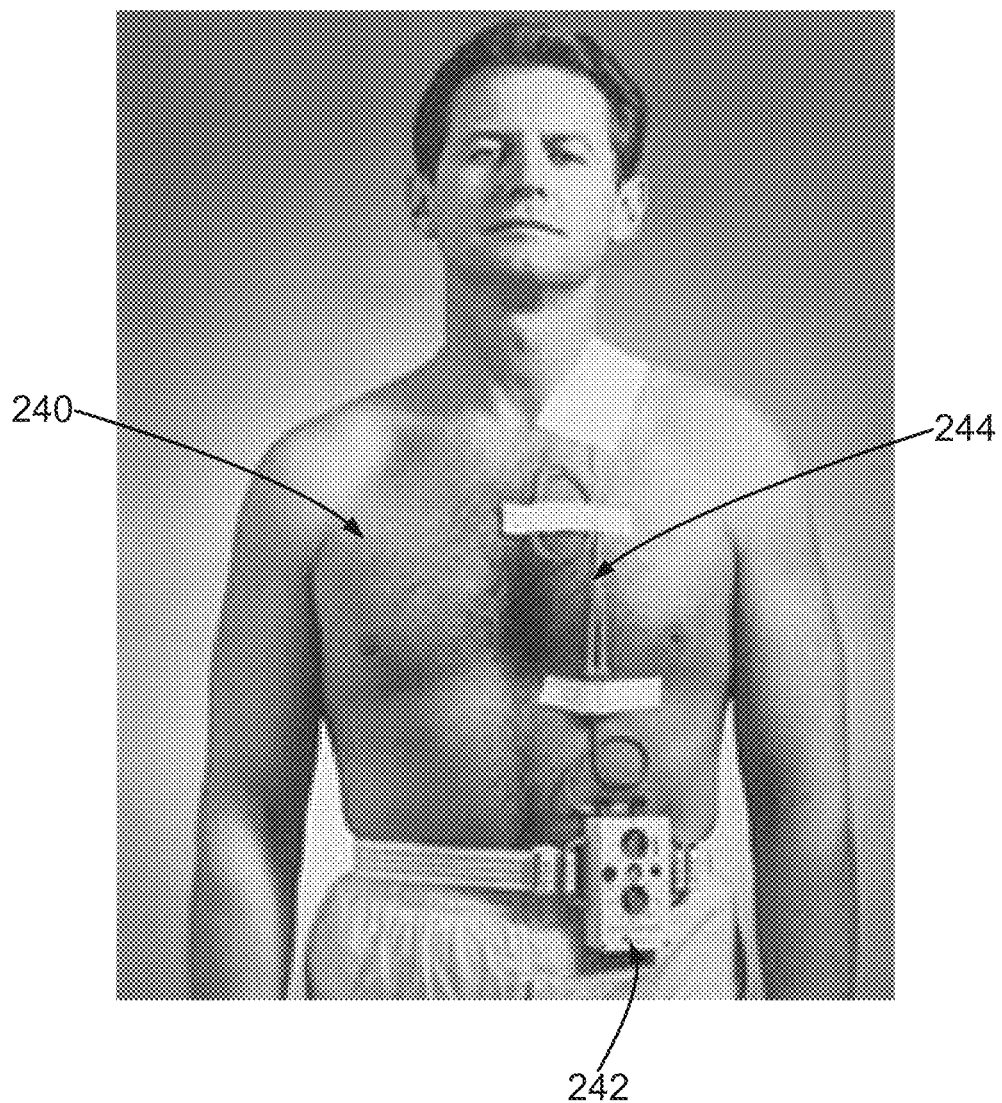
FIG. 2E is a simplified illustration of apparatus for analyzing an electrogram according to an example embodiment of the invention.

Reference is now made to FIG. 2E, which is a simplified illustration of apparatus for analyzing an electrogram according to an example embodiment of the invention.

FIG. 2E shows a schematic depiction of a chest 240, with a device 242, also termed a can, external to the chest 240, and with one or more electrodes 244 electrically connecting the device 242 with one or more electrogram signal pickup locations located within the subject's body (not shown).

FIG. 2E depicts an example embodiment in which the device 242 is external to the subject's body, while the electrodes 244 extend to one or more electrogram signal pickup locations located within the subject's body (not shown).

In some embodiments the device 242 is not necessarily attached to the subject's body.

In some embodiments electrodes (not shown) are entirely implanted with the subject's body, and a device (not shown) inside the subject's body sends wireless signals to a receiver (not shown) outside the subject's body.

Figure 2F:
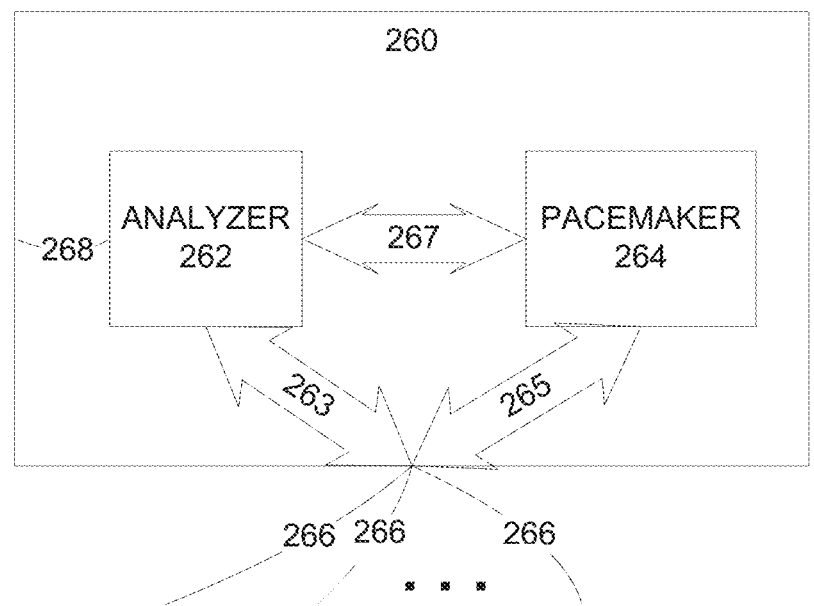
FIG. 2F is a simplified illustration of apparatus for detecting myocardial ischemia using analysis of high frequency components of an electrogram according to an example embodiment of the invention.

Reference is now made to FIG. 2F, which is a simplified illustration of apparatus for detecting myocardial ischemia using analysis of high frequency components of an electrogram according to an example embodiment of the invention.

FIG. 2F shows a schematic depiction of an implantable device 260, which includes an HF electrogram analyzer 262 and a pacemaker 264. In FIG. 2F the HF electrogram analyzer 262 optionally shares one or more electrodes 266 with the pacemaker 264. The analyzer 262 is optionally connected 263 to the same electrodes 266 to which the pacemaker 264 is also connected 265.

FIG. 2F depicts an example embodiment in which the analyzer 262 shares the can 260 with a pacemaker 264, and also shares the electrodes 266.

In some embodiments, the analyzer 262 is optionally connected 268 to a body of the can 260.

In some embodiments, the analyzer 262 optionally communicates with the pacemaker 264, for example in order to receive a signal when the pacemaker 264 sends a pacing signal.

Figure 2G:
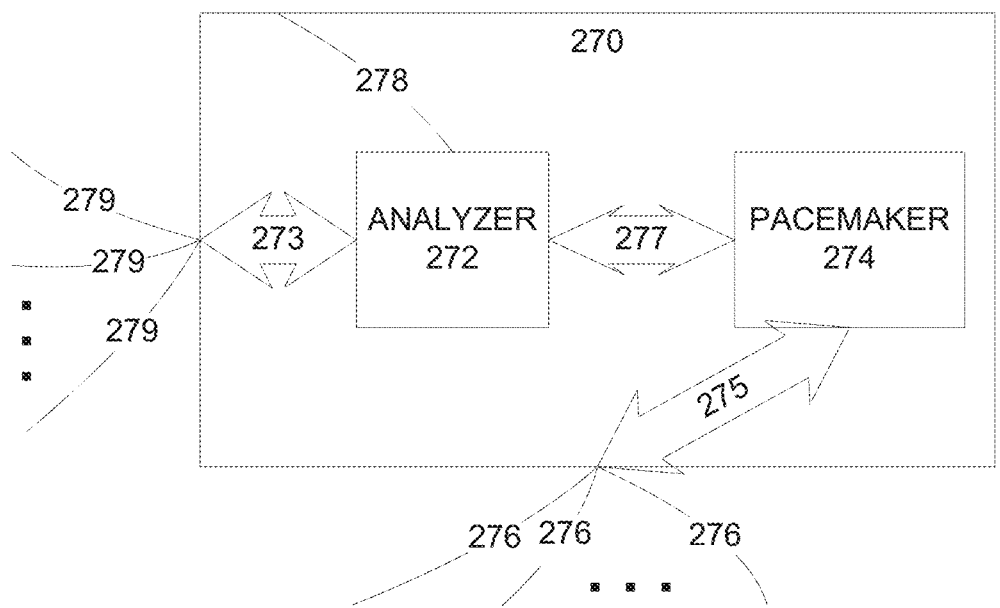
FIG. 2G is a simplified illustration of apparatus for detecting myocardial ischemia using analysis of high frequency components of an electrogram according to an example embodiment of the invention.

Reference is now made to FIG. 2G, which is a simplified illustration of apparatus for detecting myocardial ischemia using analysis of high frequency components of an electrogram according to an example embodiment of the invention.

FIG. 2G shows a schematic depiction of an implantable device 270, which an HF electrogram analyzer 272 shares with a pacemaker 274. In FIG. 2G the HF electrogram analyzer 272 is connected 273 one or more electrodes 279 not shared with the pacemaker 274, and the pacemaker is connected 275 to one or more electrodes 276 not shared with the analyzer 272.

FIG. 2G depicts an example embodiment in which the analyzer 272 shares the implantable device 270 with the pacemaker 274, and does not also share the electrodes.

In some embodiments, the analyzer 272 is optionally connected 278 to a body of the can 270.

In some embodiments, the analyzer 272 optionally communicates with the pacemaker 274, for example in order to receive a signal when the pacemaker 274 sends a pacing signal.

The present invention, in some embodiments thereof, relates to quantification of high frequency signals of the electrogram within a setting of an implantable device, and/or intracardiac electrodes and/or intracoronary electrodes.

The term endocardiac electrode refers to electrodes which are placed in the heart and typically used for mapping, and the term intracardiac electrodes refers more to single lead electrodes for pacing and/or sensing.

The term epicardial electrode refers to electrodes which are placed on a heart, beneath the pericardium.

In various embodiments, endocardiac electrode(s), and/or intracardiac electrode(s) and/or epicardial electrode(s) are used.

In various embodiments, monopolar electrodes and/or bipolar electrodes and/or multipolar electrodes or a mix thereof are used.

In some embodiments the implantable device has an independent sensing and analysis device, even if contained within a can of a pacemaker.

In some embodiments the implantable device transmits signals by wireless transmission to a receiver located outside a body of a subject in which the device is implanted. In some embodiments the transmitted signal includes raw data. In some embodiments the transmitted signal includes results of an analysis and/or an alert signal. In some embodiments the implantable device transmits signals by a wired connection to a receiver located outside a body of a subject in which the device is implanted.

In some embodiments the alert is an alert sent to a human and/or to a computer circuit and/or program and/or receiver.

In some embodiments the implantable device is used in conjunction with other implantable devices such as a pacemaker, an implantable cardioverter defibrillator (ICD), a neural stimulator, an implantable pump, a stent, artificial valves, or a cardiac resynchronization therapy (CRT) device.

In some embodiments the implantable device shares a can and/or electrodes with the above-mentioned implantable devices.

In some embodiments the implanted device optionally uses implantable electrodes for sensing an electrogram. Such electrodes are optionally placed on a surface of the device (which is implanted inside the subject's body, optionally close to the heart), and/or removably attached to the device and placed in proximity of a heart in intracardiac or/and endocardial and/or intracoronary positions.

In some embodiments the device optionally measures an electrogram signal between 2 electrodes and/or between several pairings of electrodes.

In some embodiments the device optionally measures an electrogram signal between an electrode and a location on a can of the implantable device—optionally on a surface of the implantable device.

In some embodiments, high frequency analysis of the QRS complex segment of the electrogram is optionally used for detecting myocardial ischemia. The high frequency analysis optionally calculates one or more parameters based on the high frequency electrogram signal.

In some embodiments, detecting ischemia, or calculating a parameter based on the high frequency electrogram signal which can potentially indicate ischemia, optionally causes sending an alert to a pacemaker.

In some embodiments, detecting ischemia, or calculating a parameter based on the high frequency electrogram signal which can potentially indicate ischemia, occurs inside an implantable device such as a pacemaker or other implantable device.

In some embodiments, a P-wave interval is evaluated for detection of atrial fibrillation onset and/or for indication of potential future onset of atrial fibrillation, and/or an irregular propagation of an action potential in a cardiac atria, and/or atrial tachycardia, and/or atrial bradycardia, and/or atrial arrhythmia.

In some embodiments, upon detection of onset of atrial arrhythmia, or indication of potential future onset of atrial arrhythmia, a signal is produced to initiate anti-arrhythmia pacing.

In some embodiments, upon detection of onset of atrial fibrillation, or indication of potential future onset of atrial fibrillation, a defibrillator is optionally instructed to charge.

In some embodiments, upon detection a condition such as onset of atrial fibrillation, and/or indication of potential future onset of atrial fibrillation, and/or an irregular propagation of an action potential in a cardiac atria, and/or atrial tachycardia, and/or atrial bradycardia, and/or atrial arrhythmia, a signal is produced to stop a pacemaker from producing signals which induces the above condition(s).

In some embodiments the apparatus is optionally tuned so as to reduce and/or stop a detected condition.

In some embodiments, ischemia is detected by detecting a reduction in HF ECG intensity, and/or a change in amplitude of an ST segment of the HF ECG signal. Following detection of ischemia, for example, the reducing/stopping optionally includes reducing a pacing rate by a preset number of beats-per-minute or by a preset percentage of the heart rate. In some embodiments the reduction is optionally adjusted by measuring an indication of the ischemia level, and optionally reducing the pacing rate in a closed-loop feedback manner which monitors the indication of the level of ischemia and sets the pacing rate accordingly.

In some embodiments, atrial arrhythmia is detected by a significant change in the P wave HF ECG morphology. Optionally, upon detecting onset of atrial arrhythmia, the pacing rate is manipulated to overcome the atrial arrhythmia. By way of a non-limiting example, such a manipulation includes increasing the pacing rate to control the rate and then gradually decrease the rate back to normal values.

For atrial fibrillation, for example, the reducing/stopping optionally includes modulation of a pacing signal so as to overcome the atrial fibrillation, for example by increasing the heart rate to gain control over the heart-rate, optionally followed by reducing the heart-rate to reach lower values. In some embodiments the reducing/stopping is optionally done by a high atrial pacing, which optionally takes over a natural fibrillation rate, optionally followed by decreasing the atrial pacing rate.

In some embodiments an electrogram signal which is detected to have a high HF content and/or a fluctuation in HF content of the P wave optionally causes a determination of a potential for developing arrhythmia. The determination may optionally cause producing a warning.

In some embodiments the following parameters are calculated based on the high frequency electrogram signal and high frequency ECG analysis:
- an RMS of the high frequency signal of the QRS complex, which typically decreases during ischemia;
- detection and quantification of a reduced amplitude zone (RAZ) in the high frequency signal of the QRS complex.

The high frequency electrogram is optionally measured in various configurations allowing for the analysis of electrical activity in multiple vectors according to the location of the electrodes relative to the device's can and/or between pairs of electrodes and/or combinations of electrodes.

Locations for the Implantable Device

The implantable device for the electronics for performing at least the pickup of the HF signals, as well as optionally the pickup of regular-frequency ECG signals, in different embodiments, may be found as:
- an implanted device, by way of a non-limiting example such as depicted in FIGS. 2A, 2B and 2D;
- an external device, by way of a non-limiting example such as depicted in FIG. 2E.

In some embodiments an implanted device is optionally included in a pacemaker can, optionally a smart pacemaker.

In some embodiments an implanted can is optionally a can implanted separately from an existing pacemaker, if any.

In some embodiments the can optionally serves for HF electrogram signal pickup, and transfers the signals to an external analysis unit. In some embodiments the transfer of the signals is optionally performed wirelessly. In some embodiments the transfer of the signals is optionally performed by wire.

Internal/External Electrodes

In some embodiments the pickup electrodes are implanted electrodes common with pacemaker electrodes.

In some embodiments the pickup electrodes are implanted electrodes separate from pacemaker electrodes.

In some embodiments the pickup electrodes are inserted into a subject's body via a catheter, and optionally used while the catheter is inside the subject's body, without being implanted.

Electrode Locations

In various embodiments the pickups are located in various locations, such as, by way of some non-limiting examples:
- a right atrium (RA);
- a right ventricle (RV);
- a left ventricle (LV);
- a coronary sinus (CS);
- an epicardial location; and
- an electrode located in the chest.

Internal/External Analysis

In some embodiments analysis of the HF electrogram signals is performed within an implanted can.

In some embodiments analysis of the HF electrogram signals is performed externally of a subject's body.

During Angiogram/Angio-Stent

In some embodiments monitoring and/or analysis of the HF electrogram signals is performed during a procedure in which electrodes are inserted into a subject's body, such as, by way of a non-limiting example, during an angiogram, with electrodes inserted via catheter.

Detecting the QRS Complex

In some embodiments, a temporal location of the QRS complex is optionally detected by analyzing a signal from an electrode in the right atrium.

A natural heart pacing starts at the right atrium.

In some embodiments detecting onset of a pulse optionally provides an indication when to start recording at a HF sampling rate.

In some embodiments HF sampling is optionally synchronized with a pacemaker pacing pulse.

In some embodiments an estimation is made as to when a next QRS complex signal is expected based on timing and rate of previous heart beats.

HF Sampling in a Sub-Portion of the Cardiac Cycle

The terms cardiac cycle portion, cardiac cycle sub-portion and cardiac cycle segment are used interchangeably in the specification and claims.

In some embodiments, especially implantable embodiments, power and current consumption may impose constraints on the device and/or method of detection and monitoring of myocardial ischemia. In such embodiments it is preferable to save in power consumption of the device.

In some embodiments, to facilitate the saving, a specific mode of the device is optionally configured to sample the electrogram at a high sampling rate, e.g. 1000 samples per second, only during specific portions of the signal or of the cardiac cycle, e.g. during and around the QRS complex. At other times, which typically constitute more than 50% and up to 90% of the cardiac cycle, the signal may be sampled at a lower frequency, for example, fewer than 150 samples per second. In some embodiments, the sampling rate is lowered even further, and/or suspended altogether.

In some embodiments the device is optionally configured to perform HF sampling only during, by way of some non-limiting example:
   the QRS complex interval;
   the P wave interval;
   the T wave interval;
   the Q wave interval:
   the R wave interval: and
   the S wave interval.

In some embodiments, a beginning and/or and end of the segment of the cardiac cycle is defined to start and/or end based, by way of some non-limiting examples, on one or more of:
   detection of a specific point in a cardiac cycle, optionally using analysis of the HF electrogram and/or a low frequency ECG;
   a timing offset from a trigger such as the above specific point, for example a P wave maximum plus 10 milliseconds; and
   a timing offset from a trigger such as a pacing signal, for example a P wave maximum plus 10 milliseconds.

Generally, high frequency signals are analyzed in a range of frequencies between 100 and 1000 Hz, and low frequency ECG signals are analyzed in a range of frequencies between 0.05 and 100 Hz. In some embodiments analysis of the high frequency signal samples is optionally performed for a frequency between 100 and 300 Hz, optionally with signals sampled at a rate of 1000 Hz or more. In some embodiments analysis of the high frequency signal samples is optionally performed for a frequency above 500 Hz.

In some embodiments an intracardiac electrogram is measured during a QRS complex with a high sampling rate, and during a rest of the cardiac cycle using low sampling rate. Some non-limiting example include a high sampling rate greater than 500 samples per second, and even greater than 1,000 samples per second. Some non-limiting example include a low sampling rate greater than 150 samples per second, lower than 100 samples per second, and even lower than 60 samples per second.

In some embodiments detecting the QRS complex is performed by detecting the QRS complex in a low frequency electrogram, that is, detecting the QRS complex in a regular ECG.

In some embodiments detecting the QRS complex is performed by detecting the QRS complex by analyzing a high frequency electrogram.

Cleaning Up the HF Signal

The high frequency signal used for detecting myocardial ischemia may be relatively low in amplitude, even for intracardiac signals. In some embodiments the HF signal is optionally aligned and averaged over several QRS complexes which are close in time. Such an averaging procedure potentially increase the SNR (Signal to Noise Ratio), potentially enabling a more accurate analysis. A non-limiting example method of cleaning up the HF signal is described in above-mentioned U.S. Pat. No. 8,626,275.

In some embodiments the high frequency electrogram signals are optionally aligned based on one or more of the following:
   a time of depolarization onset of the heart as detected in an electrogram, optionally an electrogram picked up by an electrode in the heart, preferably in the right atrium; and
   a time of pacing by a pacemaker in the Right Atrium (RA), Right Ventricle (RV) or Left Ventricle (LV).

Figure 2H:
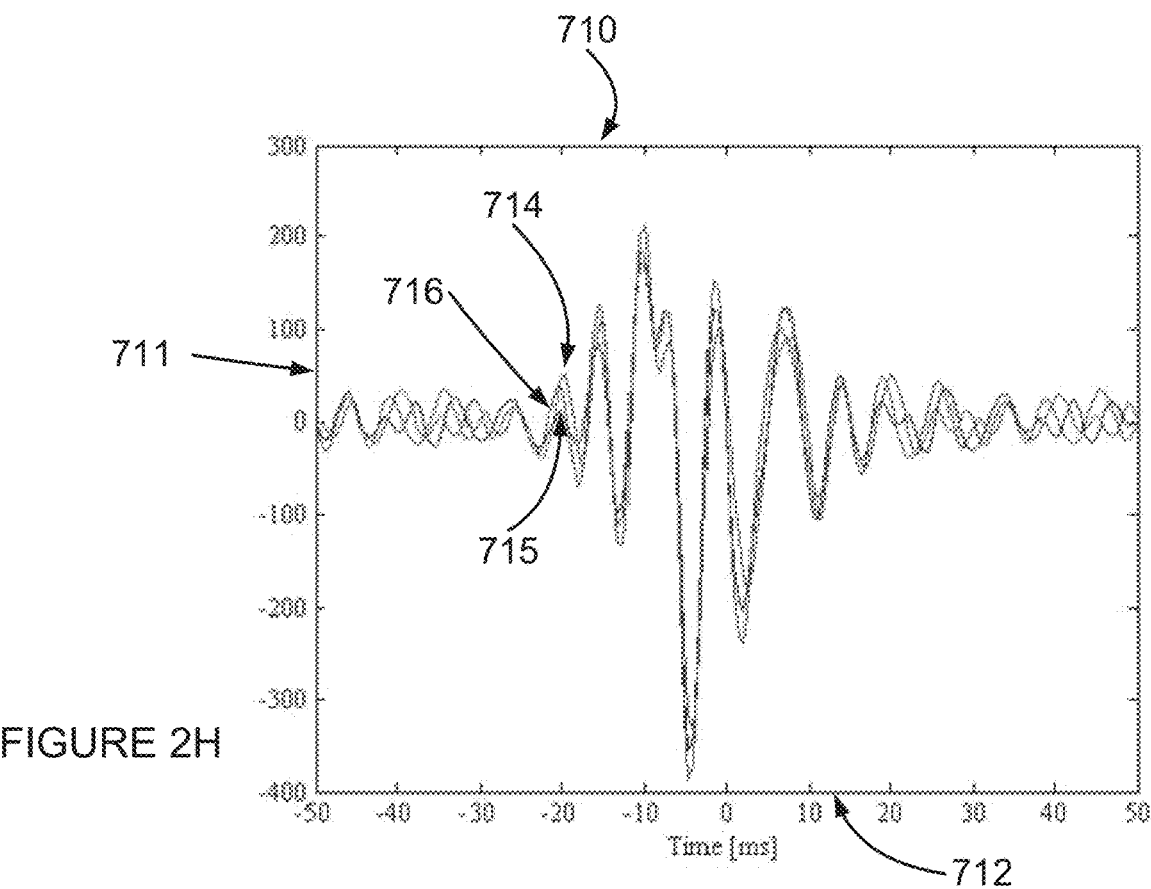
FIGS. 2H and 2I are graphs showing good correlation and bad correlation of HF signals according to an example embodiment of the invention.
Figure 2I:
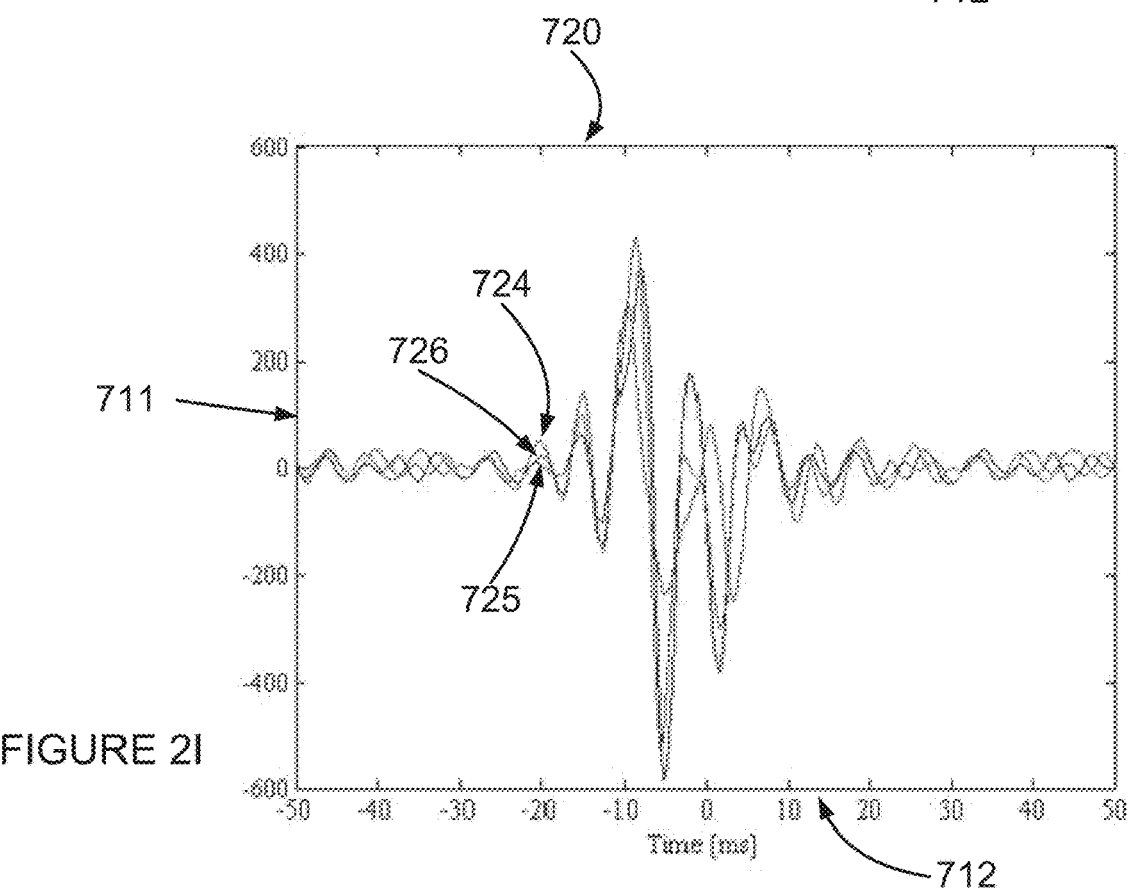

Reference is now additionally made to FIGS. 2H and 2I, which are graphs 710 720 showing good correlation and bad correlation of HF signals 714 715 716 724 725 726 according to an example embodiment of the invention.

FIG. 2H depicts the graph 710 of the HF signals 714 715 716 showing the HF signals 714 715 716 having a relatively good correlation with each other.

FIG. 2I depicts the graph 720 of the HF signals 724 725 726 having a relatively worse correlation with each other.

It is additionally noted that the graphs 710 720 have a Y-axis 711 of arbitrary correlation units, and an X-axis 712 of time in milliseconds.

FIGS. 2H and 2I illustrate that HF signals may be aligned with each other, optionally by shifting the HF signal in time forward and backward to achieve an optional correlation, and/or a correlation coefficient value which is above a specific correlation coefficient threshold. A non-limiting example of such a specific correlation coefficient threshold is optionally 0.7, or 70%, and a range of 0.5 (50%) to 0.95 (95%) is a range contemplated for such values In some embodiments, measuring correlation between HF electrogram signals is optionally used to detect noisy HF signals, and optionally to disregard the noisy signals.

In some embodiments, the alignment may optionally be performed based on aligning low-frequency electrogram signals.

Figure 2J:
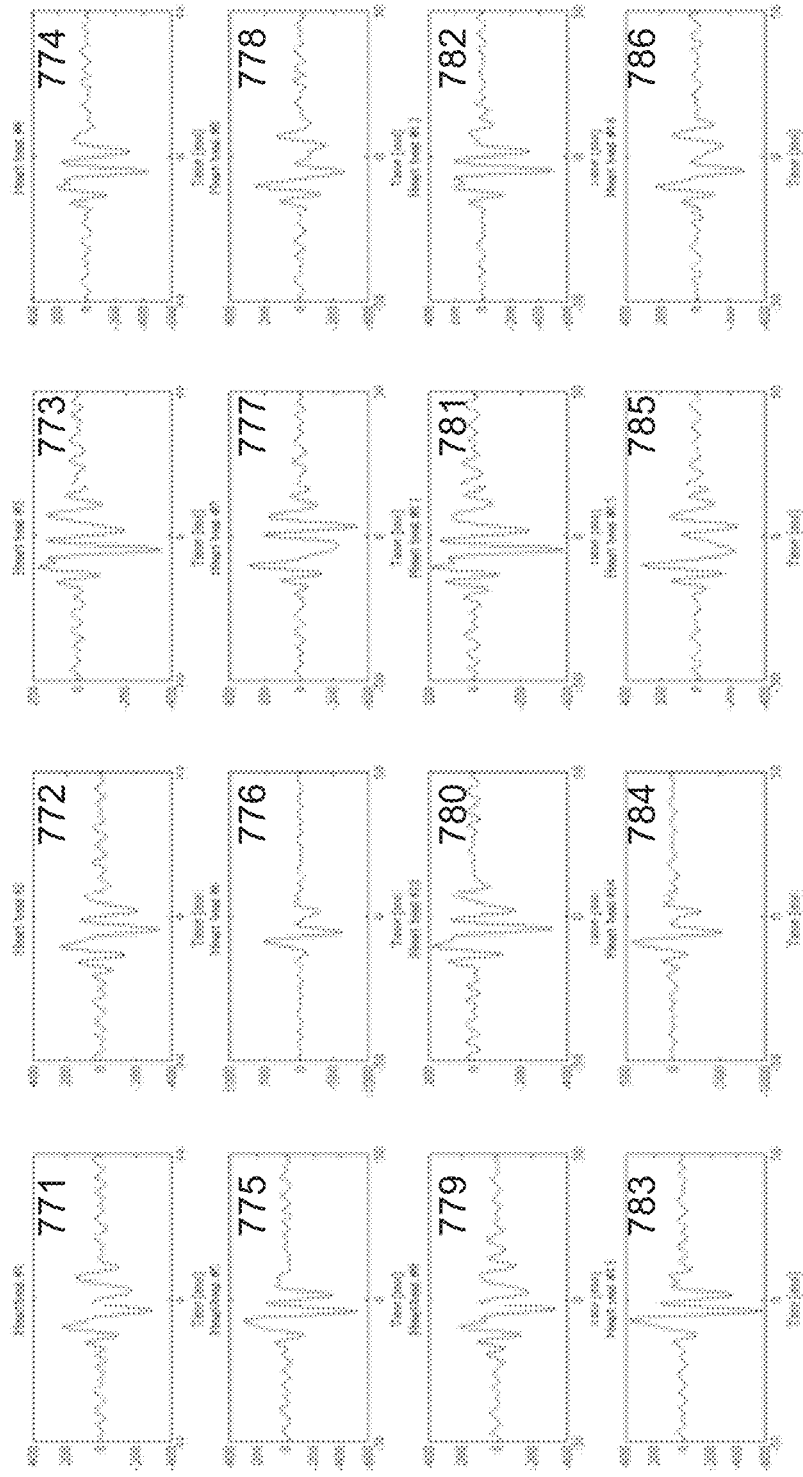
FIG. 2J depicts graphs of HF signals of 16 different QRS complexes according to an example embodiment of the invention.

Reference is now additionally made to FIG. 2J, which depicts graphs 771-986 of HF signals of 16 different QRS complexes according to an example embodiment of the invention.

The graphs 771-986 depict HF signals of consecutive QRS complexes, depicting some signals which appear clean and lend themselves well to be correlated to each other, and some which appear noisier and are not so well correlated to each other.

In some embodiments, performing correlation between two electrogram signals which have been sampled for different heartbeats is optionally performed by performing a mathematical correlation function between two vectors which contain sample values of amplitudes of the two electrogram signals. A result of the correlation is a correlation coefficient.

In some embodiments correlation is performed at different time-shifts between the two vectors, and a maximum value of the correlation coefficient is optionally determined.

In some embodiments, a time-shift corresponding to the maximum value is determined to be a time-shift desired for aligning the two electrogram signals.

Figure 2K:
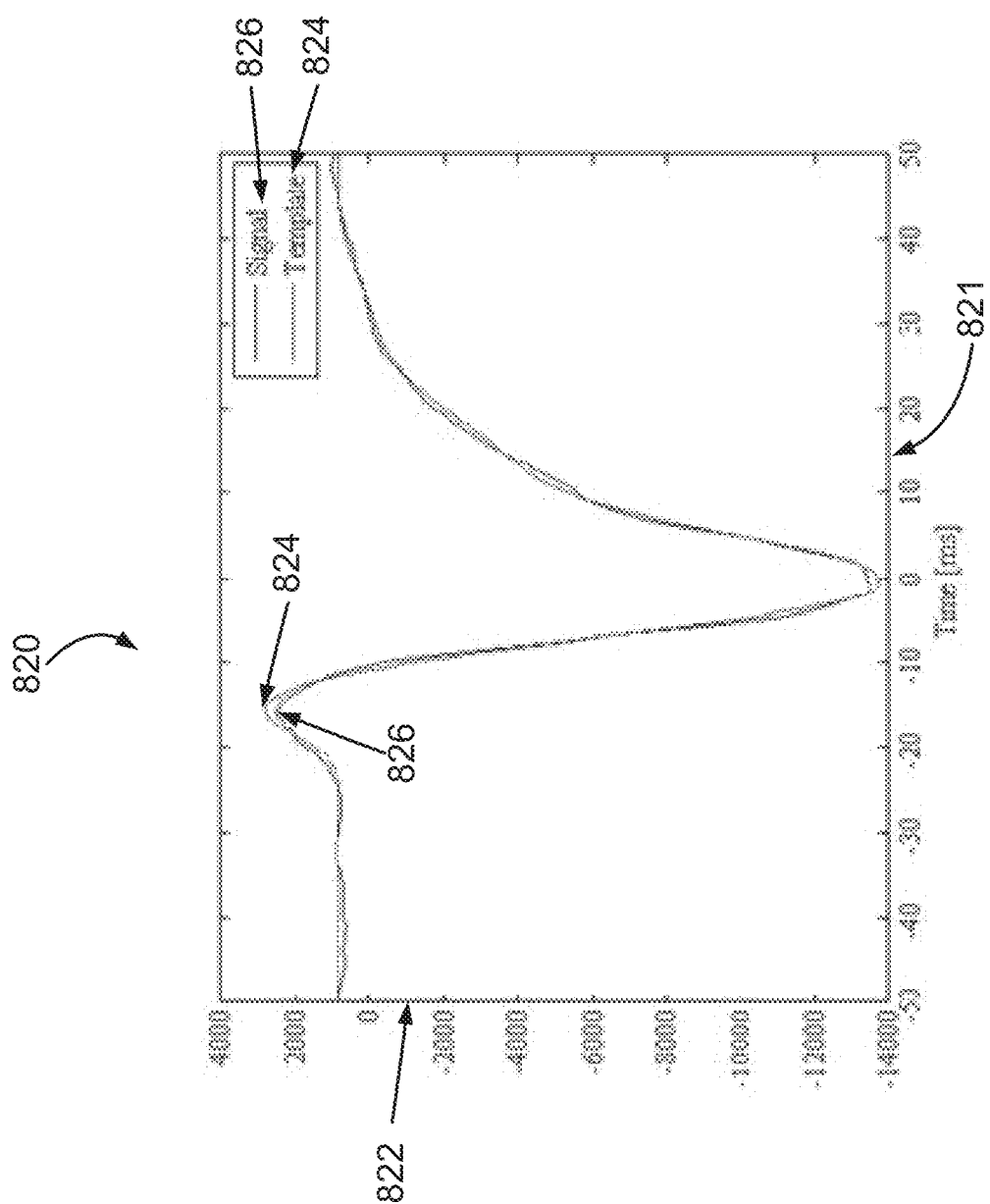
FIG. 2K depicts a graph of alignment of an unfiltered electrogram signal to a template according to an example embodiment of the invention.

Reference is now additionally made to FIG. 2K, which depicts a graph 820 of alignment of an unfiltered electrogram signal 826 to a template 824 according to an example embodiment of the invention.

The graph 820 depicts an electrogram signal 826 and an inherent electrogram signal which acts as a template 824 for a QRS complex of a heartbeat, both without filtering for HF frequencies. The electrogram signal 826 and the template 824 have a shape like a familiar low-frequency QRS complex signal because low frequency components of an electrogram signal typically have a much larger amplitude than high frequency components of the electrogram signal.

The graph 820 has a Y-axis 822 of voltage in microvolt units, and an X-axis 821 of time in milliseconds.

FIG. 2K depicts an inherent shape of the electrogram signal as portrayed by the template 824.

In some embodiments, an unfiltered electrogram signal such as the unfiltered electrogram signal 826 is optionally used to align electrogram signals, including HF signals, that is, to determine a time shift between electrogram signals from different heartbeats, so as to compare the electrogram signals to each other and/or to a baseline.

In some embodiments, a filtered low-frequency electrogram signal (not shown) is optionally used to align the electrogram signals.

In some embodiments, the alignment is based on one of the alignment methods described above, and it is high-frequency components of the electrogram signals which are then compared to each other and/or to a baseline.

In some embodiments the QRS complex template 824 is optionally produced by curve fitting a mathematical function to an inherent electrogram signal or to a QRS complex section of an inherent electrogram signal. The inherent QRS complex signal is optionally an exemplary QRS complex signal, optionally produced from one or more unfiltered, or low-frequency electrogram signals or QRS complex sections of such electrogram signals.

Figure 2L:
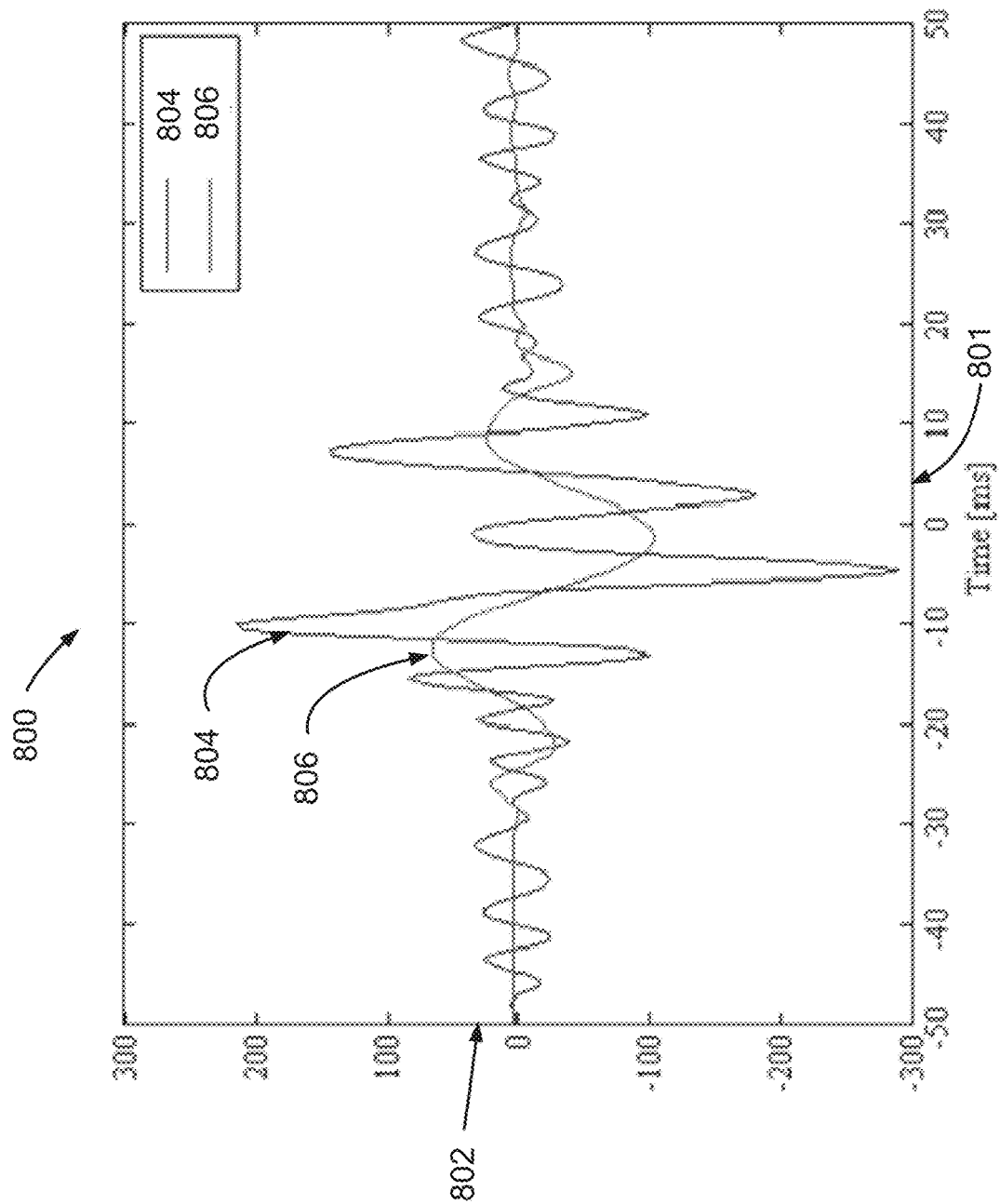
FIG. 2L is a graph depicting an HF portion of an inherent electrogram signal and an actual HF signal, according to an example embodiment of the invention.

In some embodiments, an inherent HF signal is calculated. Such an inherent HF signal is depicted in FIG. 2L, and described below.

In some embodiments the curve fitting optionally involves calculating a number of coefficients for the mathematical function to fit the inherent HF signal.

In some embodiments the mathematical function is a polynomial function.

In some embodiments the mathematical function is for example cubic spline.

In some embodiments the number of coefficients for producing the template 824 is typically 20 or more, or between 5 and 30, and even a range of 3, 5, 10, 20, 50 or 100 coefficients are contemplated.

In some embodiments the QRS complex template 824 is optionally produced by averaging a number of electrogram signals, by way of a non-limiting example such as the electrogram signal 826, over several heartbeats.

Reference is now additionally made to FIG. 2L, which is a graph 800 depicting an HF portion of an inherent electrogram signal 806 and an actual HF signal 804, according to an example embodiment of the invention.

The HF portion of an electrogram signal, including both the inherent electrogram signal 806 and the actual HF signal 804 is potentially less dependent on noise originating from a patient's movement, and potentially supports better detection and/or monitoring of a patient's heart condition.

FIG. 2L depicts the HF portion of the inherent electrogram signal 806, and the actual HF signal 804, either of which can be compared to a baseline (not shown) and potentially detect changes in a patient's physiological condition.

The graph 800 has a Y-axis 802 of millivolt units, and an X-axis 732 of time in milliseconds.

In some embodiments analysis of the high frequency signal is optionally filtered for a frequency above 500 Hz.

Noise

In some embodiments, a heartbeat period which produces a noisy electrogram signal is discarded from use in the analysis.

In some embodiments determining that an electrogram signal is noisy is optionally performed based on a high-frequency-filtered electrogram signal. In some embodiments determining that an electrogram signal is noisy is optionally performed based on a low-frequency-filtered electrogram signal. In some embodiments determining that an electrogram signal is noisy is optionally performed based on an electrogram signal which includes both high and low frequencies.

In some embodiments, detecting a noisy HF electrogram signal is optionally performed by measuring noise in a quiet segment of an HF electrogram signal, such as in an ST segment, and/or between a T segment and a following P segment, and/or in a T segment, and/or simply outside of a QRS complex segment.

In some embodiments, detecting a noisy HF electrogram signal is optionally performed by calculating a correlation coefficient of the electrogram signal to an inherent electrogram signal, and comparing the correlation coefficient to a threshold value.

In some embodiments, a threshold level for determining that a HF electrogram signal is noisy is measuring noise, by way of a non-limiting example RMS noise of less than 1 microvolt. In some embodiments, the RMS noise threshold for the HF signal is optionally between 0.2 microvolts and 2 microvolts.

In some embodiments, upon detecting an electrogram signal having a noise value greater than the noise threshold, the signal is discarded from use for any purpose. In some embodiments, the noisy signal is discarded from use in determining a patient's condition. In some embodiments, a noisy signal is tagged as noisy, and saved associated with the tag.

The Breathing Cycle

The terms breathing cycle portion and breathing cycle segment are used interchangeably in the specification and claims.

A linkage between a breathing cycle and heart rate is known in the literature and referred to as Respiratory Arrhythmia. The heart rate, in turn, is among the factors which govern the behavior of the high frequency ECG signal, which results in a potential coupling between analysis of high frequency ECG signals parameters and the breathing cycle.

In some embodiments the breathing cycle is optionally analyzed and comparison of high frequency ECG analysis results is optionally done between measurements taken at similar times in the breathing cycle. For example, a comparison of high frequency ECG parameters is performed between high frequency ECG parameters measured at maximum exhalation.

Figure 3:
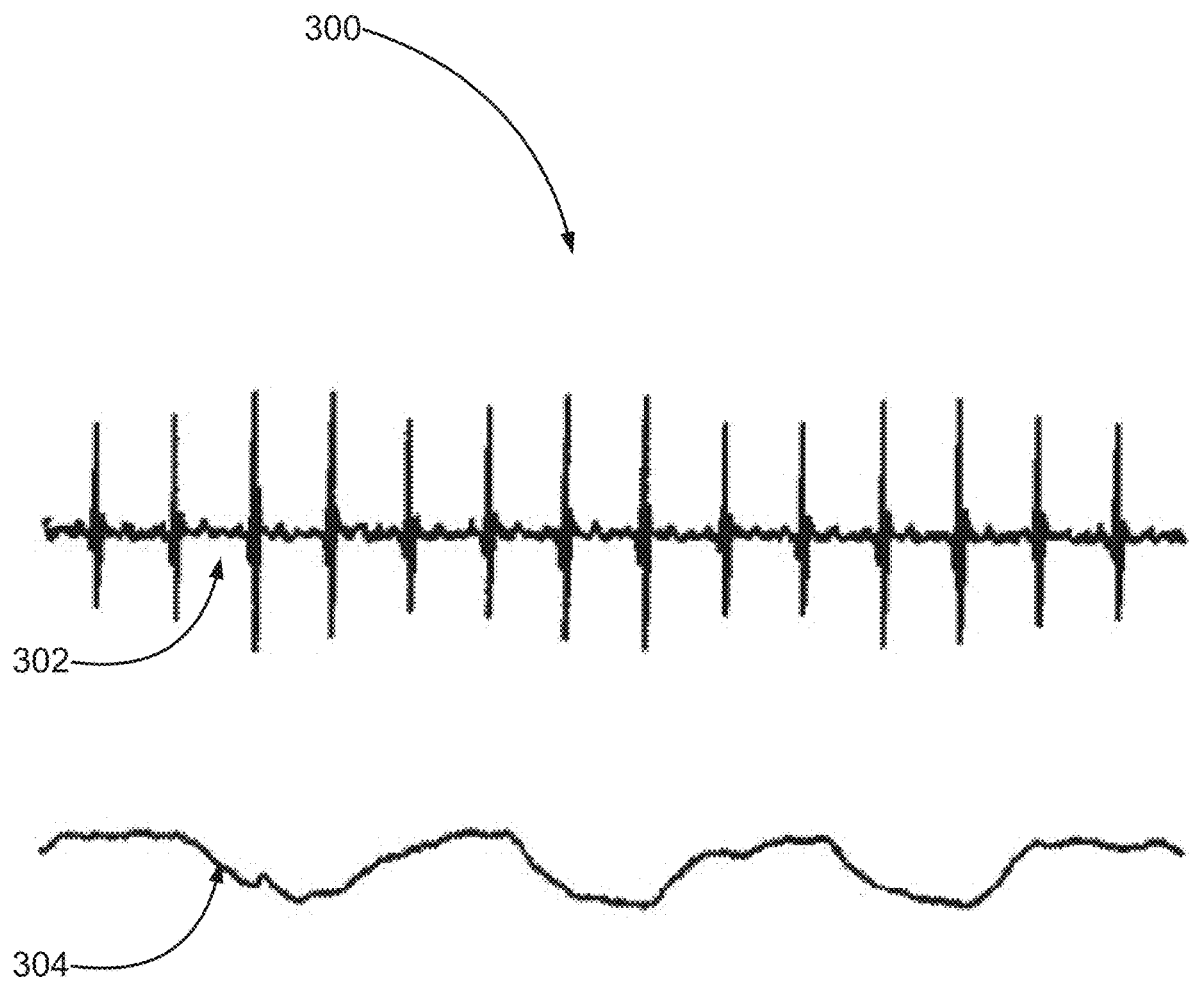
FIG. 3 is a simplified prior art illustration of effects of breathing on electrocardiogram signals.

Reference is now made to FIG. 3, which is a simplified prior art illustration of effects of breathing on electrocardiogram signals.

FIG. 3 depicts a graph 300 of respiration-induced modulation of QRS complex amplitude in a regular ECG signal. An upper trace 302 depicts an ECG trace, and a lower trace 304 depicts respiration as measured by a pneumatic respiration transducer (PRT) placed around a chest of a subject. The upper trace 302 and the lower trace 304 depict measurements over a duration of 10 seconds. The graph 300 is taken from the above-mentioned article titled "Derivation of Respiratory Signals from Multi-lead ECGs" by Moody et al.

FIG. 3 depicts and the article teaches a method for analyzing QRS complex amplitude in a regular ECG signal and respiratory actions. By way of a non-limiting example, the amplitude of the QRS complex is seen to increase and decrease in relation to the respiration.

In some embodiments, high frequency ECG parameters are measured only during a specific portion of a breathing cycle, by way of some non-limiting examples, when QRS complex amplitude is maximal or when QRS complex amplitude is minimal.

In some embodiments detecting the segment of the breathing cycle includes measuring amplitude of a QRS complex of a low frequency electrogram.

In some embodiments, high frequency ECG parameters are measured only during a specific portion of a breathing cycle, by way of some non-limiting examples, when the cardiac cycle is shorter than average or when the cardiac cycle is longer than average.

In some embodiments detecting the segment of the breathing cycle comprises measuring a duration of a cardiac cycle.

In some embodiments, high frequency ECG parameters are measured only once during a breathing cycle instead of every heartbeat. Such embodiments provide a method of potentially saving power.

In some embodiments the stages of the breathing are optionally measured by one or more motion sensors in or connected to the implanted device.

In some embodiments the stages of the breathing are optionally measured by a strap around the chest. In such embodiments the strap is optionally communicating with an analysis unit, optionally an external analysis unit using electrodes with a body, such as inserted via a catheter.

In some embodiments the stages of the breathing are optionally measured by an audio sensor. Such detection by audio sensors can potentially operate both in implantable devices and in external devices.

In some embodiments the stages of the breathing are optionally measured by a spirometric device. A spirometric device may be in a unit external to a subject's body, sending a signal to an implanted unit to enable detecting the stages of the breathing. In some embodiments, use of the stages of breathing during HF signal analysis is enabled when a signal from the spirometric device is received by the implanted device. In some embodiments, the stages of breathing are not used during HF signal measurements when a signal from the spirometric device is not received by the implanted device.

In some embodiments, detecting a portion of the breathing cycle is optionally performed by using motion sensors and analysis to detect cyclic movement of a subject's chest.

In some embodiments, the specific stages of the breathing cycle are optionally selected based on characterization of electrogram based on low frequency features such as amplitude of the QRS complex and/or a time within a cardiac cycle.

Additional Physiological Sensors

Using state-of-the-art physiological sensors such as, by way of a non-limiting example, a bioimpedance sensor such as Optivol by Medtronic, it is possible to measure physiological parameters, such as, by way of a non-limiting example, blood pressure in various loci, for example, in the pulmonary arteries. Additional non-limiting examples of physiological sensors include implantable hemodynamic monitoring using the Chronicle IHM system by Medtronic and the pressure monitor named heartPOD by St Jude Medical. Such measurements provide a potentially more accurate description of a subject's status, and potentially correlate to the High frequency ECG results as well as to other parameters relating to a given physiological conditions.

The High frequency ECG parameters may potentially have natural variations, even under normal circumstances. Gating or triggering an analysis of the HF signal based on values of physiological parameters such as blood pressure, pulse and breathing cycle, potentially render the High frequency ECG analysis more sensitive and accurate, increasing its usefulness for the indication of ischemic states and ischemic disease.

Simultaneous acquisition, and/or registration and/or analysis of High frequency ECG and additional variables (such as blood pressure, Heart rhythm and rate, ST changes, T-wave abnormalities, late potentials, T-wave alternans, etc.) potentially provide at least the following two consequences. First, the High frequency ECG is optionally analyzed and evaluated with respect to a multi-parameter state when recording a person's baseline. Second, High frequency ECG measurements are optionally made or analyzed only at certain, possibly predetermined, multi-parameter states.

In some embodiments the system also includes means for measuring and analyzing a low frequency electrogram signal. Low frequency electrogram analysis optionally includes analysis of: heart rate, ST segment changes, heart rate variability, T wave abnormalities including T-wave inversion and T-wave alternans; and QT interval.

In some embodiments, specific categories are defined, each category including a range of values for variables. The variables include results of analysis, such as values of HF electrogram analysis indexes and values of low frequency electrogram analysis; and values of physiological measurements, such as blood pressure, heart rhythm and rate, ST changes, T-wave abnormalities, T-wave alternans, etc.

In some embodiments a medical pathological condition is optionally detected when there is a consistent change in both High frequency electrogram indexes and other parameters such ST changes in a regular ECG trace, and/or a change in heart rate. When a correlation between the HF electrogram indexes and the other parameters appears more than a specific number of times in a row this is optionally an indication for ischemia. In some embodiments, when more than one, two, 5 or 10 such correlations appear per day an alert is produced.

In some embodiments, determining a baseline for use in a later comparison, in order to detect ischemia, is optionally done by continuous measurements and constant updating.

In some embodiments ischemia is detected by reaching specific high frequency ECG values. By way of example when changes in RMS values of the high frequency ECG are greater than 5%, 10%, 20%, 30%, 40%, or 50% of a reference RMS value.

In some embodiments, for a morphological index as described in above-mentioned U.S. Pat. No. 8,626,275, a change in the morphological index greater than 2%, 4%, 5%, 7%, 10%, or 15% of a reference morphological index value optionally indicates possible ischemia.

In various embodiments, reference values, also termed baseline values, are determined by various methods. Some non-limiting example methods include:

using a historical average value which was measured over a previous day, week, month or year. In some embodiments the historical average is optionally selected so as to be sensitive to heart rate and optionally to additional physiological conditions; and using a baseline value which was measured at one time during a setup period or a set up test.

In some embodiments the baseline value is optionally measured under similar conditions, such as similar heart rate (pulse) and/or similar breathing rate and/or a similar portion of a cardiac cycle and/or a similar portion of a breathing cycle.

In some embodiments acute ischemia is detected by detecting changes compared to the baseline.

In some embodiments the baseline value changes over time—e.g. a baseline measured and calculated for a window of N consecutive heartbeats once every M heartbeats, and/or every period of time such as several times an hour, a day, a week, a month.

In some embodiments acute ischemia is detected by detecting changes in HF electrogram parameters measured at a low heart rate period and at a higher heart rate period. In some embodiments that change in heart rate between the two periods is greater than 10%, 20%, 40%, 50%, 100%.

In some embodiments the change in heart rate is optionally in term of a standard deviation relative to an average and standard deviation of a population of N heartbeats.

In some embodiments, by tracking the physiological and High frequency ECG parameters of the baseline itself a slow deterioration in a subject's condition is optionally detected.

In some embodiments, the High frequency ECG parameters are used for a differential diagnosis between ventricular tachycardia (VT) and supraventricular tachycardia (SVT). During VT a morphological index and/or amplitude of the HF signal changes from beat to beat, while in SVT a change from beat to beat is typically not significant.

In some embodiments, trends of calculated values are calculated and/or stored and/or transmitted. The calculated values include, by way of some non-limiting example, regular ECG values, HF electrogram values, values as described in U.S. Pat. No. 8,626,275, and so on.

In some embodiments, correlations between calculated values are calculated and/or stored and/or transmitted.

Intracoronary Electrodes

In some embodiments, one or more intracoronary electrodes are used for acquisition of the electrogram.

In some embodiments, the intracoronary electrodes are optionally located near to a known and/or to a suspected partial or complete occlusion in an artery. The electrogram signal is optionally measured proximally and distally from the occlusion, and High frequency ECG values of the signal are optionally compared to examine differences in the electrical characteristics of the tissues proximal and distal to the occlusion. The differences potentially indicate changes in vitality and potentially indicate an ischemic condition. By way of a non-limiting example, a change in HF indexes between a point before blockage and a point after the blockage change significantly. A change in RMS HF values of greater than 5%, 10%, 20%, 30%, 40%, or 50% of a reference HF RMS value and/or a change in a morphological index by more than 1%, 2%, 3%, 4%, 5% or 6% of a reference morphological index.

Figure 4A:
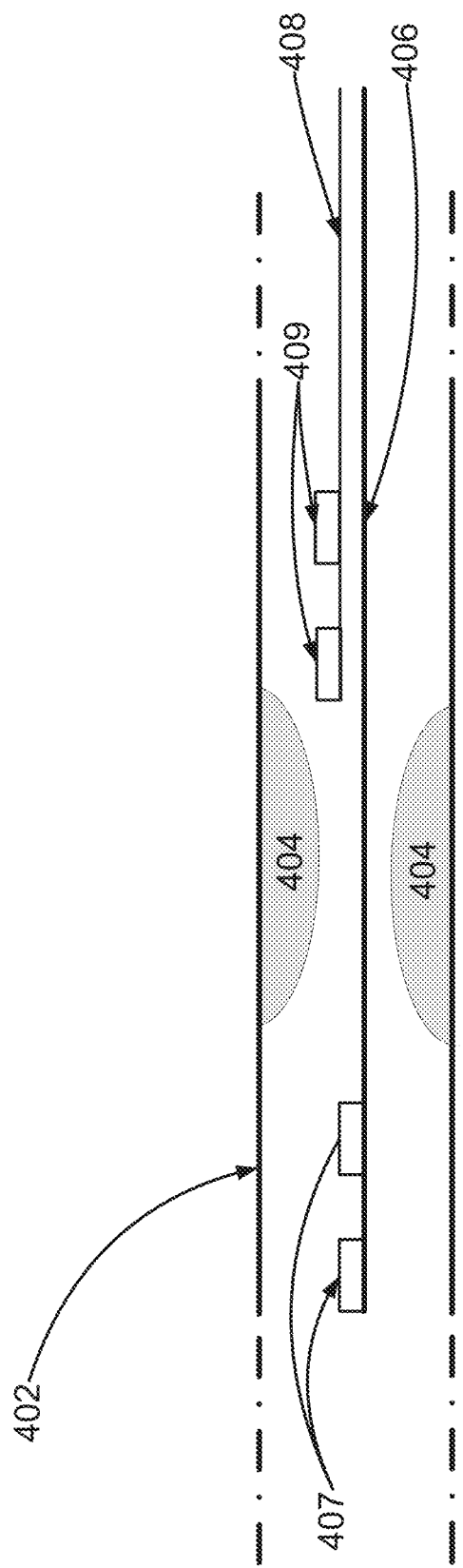
FIG. 4A is a simplified illustration of electrodes for picking up an electrogram within a blood vessel according to an example embodiment of the invention.

Reference is now made to FIG. 4A, which is a simplified illustration of electrodes for picking up an electrogram within a blood vessel according to an example embodiment of the invention.

FIG. 4A depicts an example blood vessel, an artery 402. The artery 402 has, for example, a blockage 404. A first electrode 406 having a bipolar pickup 407 is inserted up until beyond the blockage 404. A second electrode 408 having a bipolar pickup 409 is inserted until before the blockage 404.

In some embodiments one or both of the electrodes 406 408 may be monopolar electrodes (not shown) or multipolar electrodes (not shown).

In some embodiments there is a use of single electrode configuration which measures the electrogram at both locations: before and beyond the blockage 404.

Figure 4B:
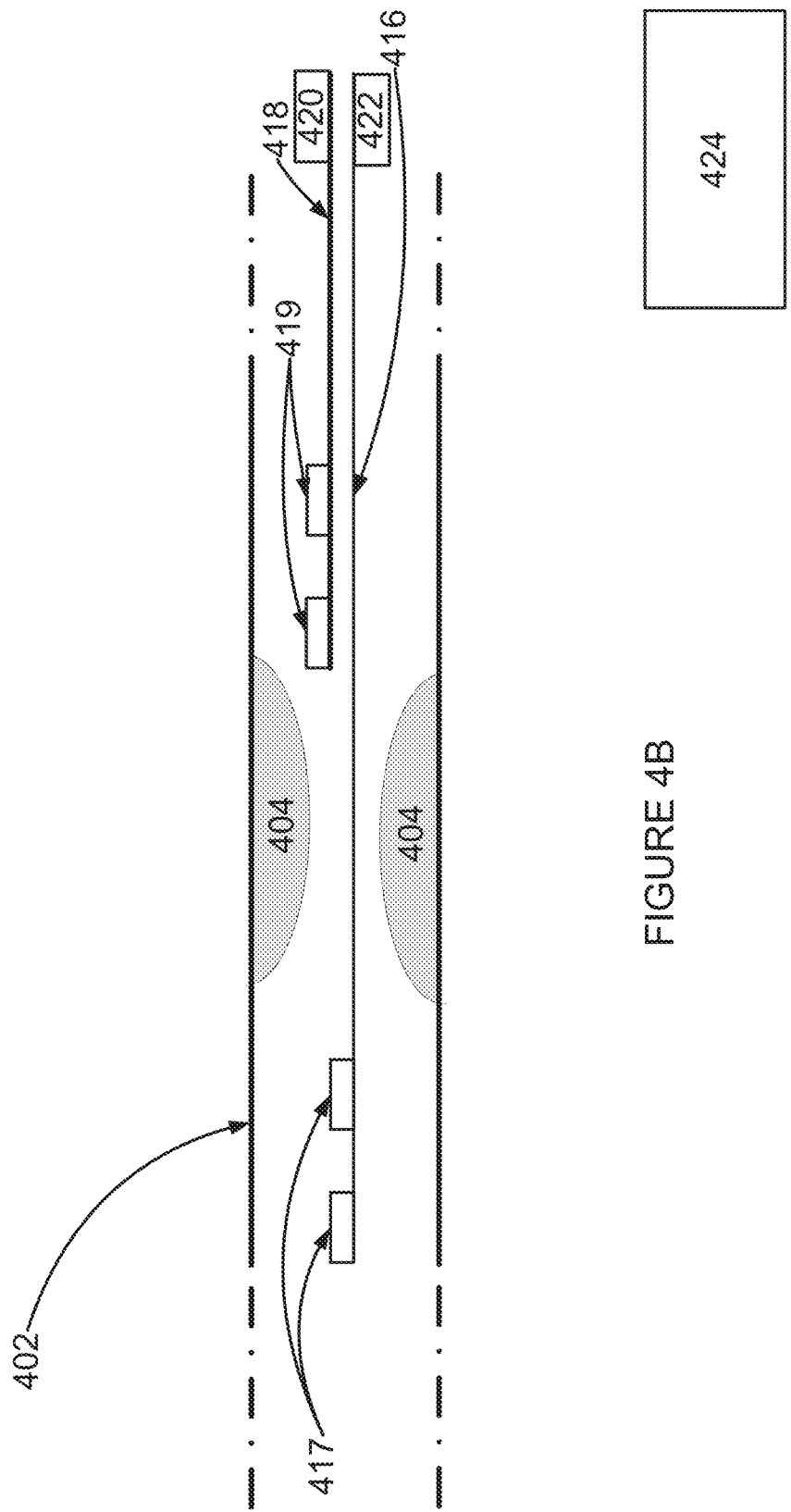
FIG. 4B is a simplified illustration of electrodes for picking up an electrogram within a blood vessel according to an example embodiment of the invention.

Reference is now made to FIG. 4B, which is a simplified illustration of electrodes for picking up an electrogram within a blood vessel according to an example embodiment of the invention.

FIG. 4B depicts an example blood vessel, an artery 402. The artery 402 has, for example, a blockage 404. A first electrode 416 having a bipolar pickup 417 is inserted up until beyond the blockage 404. The first electrode 416 also includes an electronics unit 422, which optionally communicates wirelessly with an external analyzer 424, transmitting a signal corresponding to an HF signal picked up by the bipolar pickup 417.

A second electrode 418 having a bipolar pickup 419 is inserted until before the blockage 404. The second electrode 418 also includes an electronics unit 420, which optionally communicates wirelessly with the external analyzer 424, transmitting a signal corresponding to an HF signal picked up by the bipolar pickup 419.

In some embodiments one or both of the electrodes 416 418 may be monopolar electrodes (not shown) or multipolar electrodes (not shown).

In some embodiments there is a use of single electrode configuration which measures the electrogram at both locations: before and beyond the blockage 404, at different times.

In some embodiments High frequency ECG measurement by intracoronary electrodes potentially assists in determining whether stent placement is recommended.

A change in RMS HF values of greater than 5%, 10%, 20%, 30%, 40%, or 50% of a reference HF RMS value, and/or a change in a morphological index by more than 1%, 2%, 3%, 4%, 5% or 6% of a reference morphological index optionally assist in determining whether stent placement is recommended.

In some embodiments High frequency ECG measurement by intracoronary electrodes is optionally combined with FFR (fractional flow reserve) analysis and also potentially assists in determining whether stent placement is recommended.

FFR analysis typically measures local pressure in a blood vessel. If the pressure drops below a set pressure the drop is an indication that there might be a benefit for inserting a stent. The FFR method typically evaluates whether there is a collateral blood supply or whether tissue is necrotic due to lack of blood circulation.

The above-mentioned determinations of coronary vessel condition and/or treatment may be performed both by implantable electrodes and by electrodes temporarily inserted by catheter.

The above-mentioned determinations of coronary vessel condition are potentially useful for post-revascularization evaluation of the revascularization efficacy.

In some embodiments, the coronary blood vessel in which the electrogram is measured with relation to the occlusion is a coronary artery. In some embodiments, the coronary blood vessel the coronary blood vessel is a coronary vein. In some embodiments the coronary blood vessel is the coronary sinus.

In some embodiments detection of ischemia onset is performed based on a change in one or more of the following parameters of the HF signal of an electrogram over at least one intracardiac electrode:

an RMS level of the HF signal of the electrogram;

a function of the RMS levels of the HF signal of the electrogram in different portions of the cardiac cycle, such as, for example, a P or a T portion of the cardiac cycle;

an envelope maximum of the high frequency signal of the electrogram;

a function of the envelope levels in different portions of the cardiac cycle, of the high frequency signal of an electrogram;

an envelope width of the high frequency signal of an electrogram, as described in above-mentioned U.S. Pat. No. 8,626,275;

an area of a reduced amplitude zone (RAZ) of the electrogram HF signal, as described in above-mentioned U.S. Pat. No. 8,626,275; and an area of a RAZ in the envelope of the electrogram HF Signal, as described in above-mentioned U.S. Pat. No. 8,626,275.

In some embodiments warning is provided of potential onset of an ischemic event, optionally based on a significant reduction in the HF intensity during an increase in heart rate. Optionally, reduction levels are adjusted for individual patients, and are typically 50% reduction during a heart rate increase of 30%, and/or when a patient traverses 70% of the patient's maximal heart rate. A potential scenario includes the patient experiencing a significant reduction in the HF content every time the patient has a significant heart rate increase.

In some embodiments when a system detects a repeating pattern the system increases a confidence value to produce an alert.

In some embodiments the alert optionally produces a sound alert for the patient and/or sends a message to medical personnel tracking the patient.

In some embodiments sound is produced by using a simple sound generator built into the device. In some embodiments the alert is produced by vibration of the device.

In some embodiments, for communication purposes, an implantable device includes a communication module. In some embodiments the communication module optionally transmits information through a receiving station, which in some cases optionally includes a smart phone, to a medical professional center.

In some embodiments a HF portion of an electrogram is measured using at least one intracardiac electrode.

In some embodiments the following configurations are optionally used for measuring an intracardiac electrogram HF signal:

a single monopolar electrode that measures a signal between an intracardiac electrode and a can (container) of an implantable device;

a bipolar electrode;

two intracardiac electrodes placed at different places within the heart;

one intracardiac and one epicardiac electrode; and two epicardiac electrodes.

In some embodiments a bipolar electrode, also termed a lead, is optionally used, having two electrical pickup points, which may also be termed two electrodes. In some embodiments the distance between the two electrical pickup points is 1-3 millimeters, or 1-5 millimeters, or 1-7 millimeters or 1-10 millimeters, which potentially measure a local change in an electrogram, potentially measuring a difference in the electrogram between the two adjacent electrical pickup points.

In some embodiments detection of ischemia and/or of onset of ischemia is optionally based, at least in part, on a function of RMS values of an electrogram HF signal, optionally measured using one of the above-mentioned electrode configurations.

In some embodiments detection of ischemia and/or of onset of ischemia is optionally based, at least in part, on a comparison of RMS values of an electrogram HF signal, optionally at different instances of similar heart rate values, such as, for example:

a difference between the RMS values exceeding a threshold difference value; and a ratio between the RMS values exceeding a threshold ratio value.

In some embodiments detection and differentiation between ventricular tachycardia and supraventricular tachycardia is optionally based, at least in part, on a function of RMS values of electrogram HF signal, using one of the above-mentioned electrode configurations.

In some embodiments differentiating between ventricular tachycardia and supraventricular tachycardia is optionally based, at least in part, on a comparison of RMS values of electrogram HF signal at different instances of similar heart rate values. The difference and/or the ratio of the RMS values measured, using one of the above-mentioned electrode configurations, are optionally considered for the differentiation.

By way of a non-limiting example, if at different time periods which have an approximately similar high heart rate there is a significant difference in a HF RMS value, the difference potentially indicates existence of tachycardia originating from the ventricle (VT), as described above.

In some embodiments acquisition of the high frequency electrogram signal is performed using intracoronary monopolar and/or bipolar electrodes in one or more locations relative to a complete and/or partial occlusion and/or suspected occlusion of a coronary artery. In some embodiments, the HF electrogram signal proximally and distally from an occlusion is optionally acquired and optionally compared. In some embodiments, one or more of the following parameters is optionally compared between a proximal and a distal HF electrogram signal:

a difference between RMS values at the proximal and distal locations;

a ratio between the RMS values at the proximal and distal locations; and a function of numerical characteristics of the HF signal envelopes at the proximal and distal locations.

In some embodiments detection of a difference in ischemic condition and/or vitality between two locations near a complete or partial occlusion of a coronary artery is optionally based, at least in part, on the methods and apparatus described above.

In some embodiments detection of difference in ischemic condition and/or vitality between two electrode locations near a complete or partial occlusion of a coronary artery is optionally based, at least in part, on the methods and apparatus described above, optionally also combined with results from FFR (fractional flow reserve) analysis.

In some embodiments detection of difference in ischemic condition and/or vitality between two locations near a complete or partial occlusion of a coronary artery is optionally based on the methods and apparatus described above, optionally for assisting in determining whether stent therapy is needed.

In some embodiments detection of difference in ischemic condition and/or vitality between two electrode locations near a complete or partial occlusion of a coronary artery is optionally based, at least in part, on the methods and apparatus described above, optionally for post-revascularization assessment of revascularization results and current ischemic condition.

Figure 5:
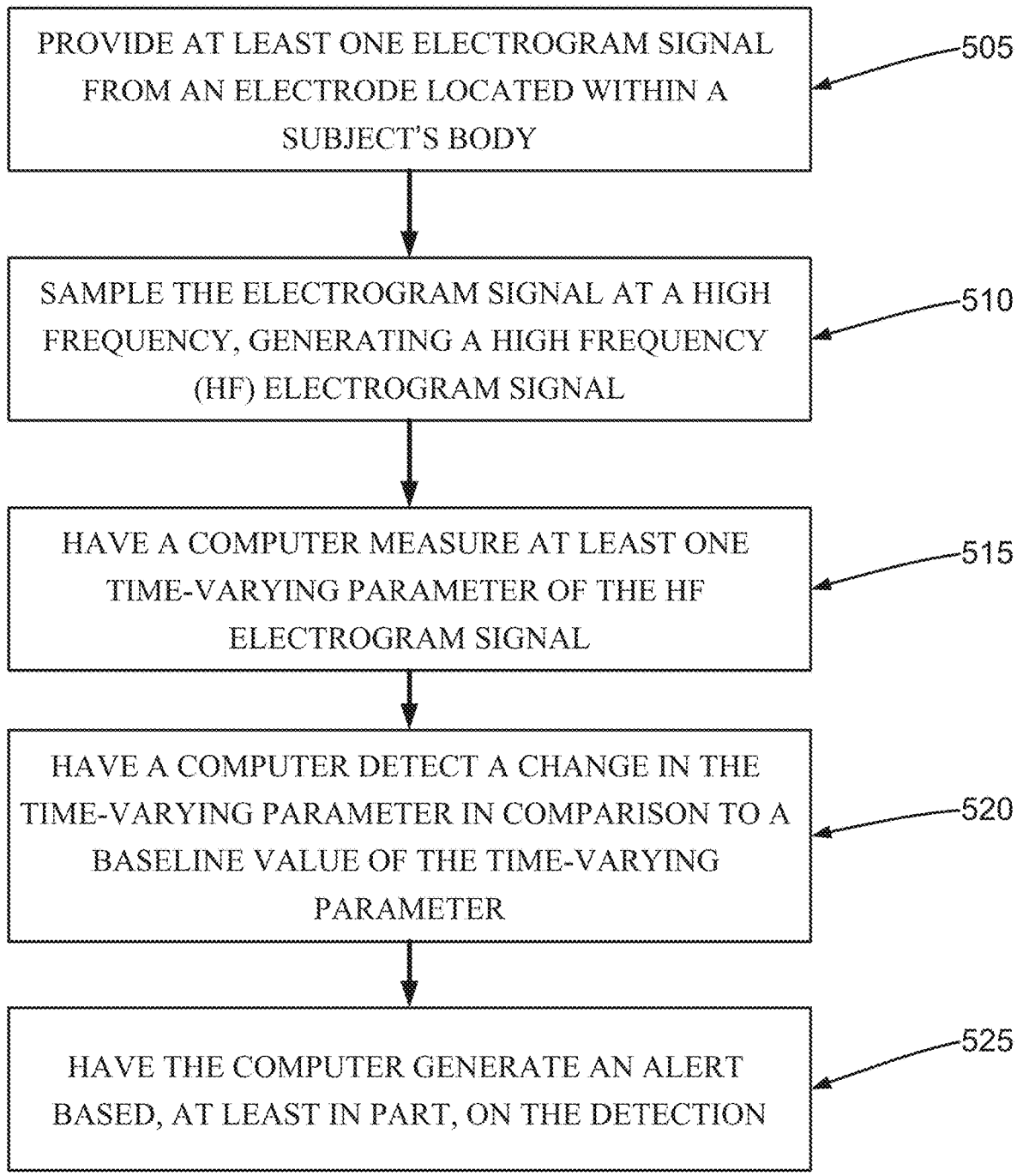
FIG. 5 is a flow chart of a method for analyzing a high frequency (HF) electrogram signal according to an example embodiment of the invention.

Reference is now made to FIG. 5, which is a flow chart of a method for analyzing a high frequency (HF) electrogram signal according to an example embodiment of the invention.

The example embodiment depicted in FIG. 5 includes:

providing at least one electrogram signal from an electrode located within a subject's body (505);

sampling the electrogram signal at a high frequency, generating a high frequency (HF) electrogram signal (510);

having a computer measure at least one time-varying parameter of the HF electrogram signal (515);

having a computer detect a change in the time-varying parameter in comparison to a baseline value of the time-varying parameter (520);

having the computer generate an alert based, at least in part, on the detection (525).

Figure 6:
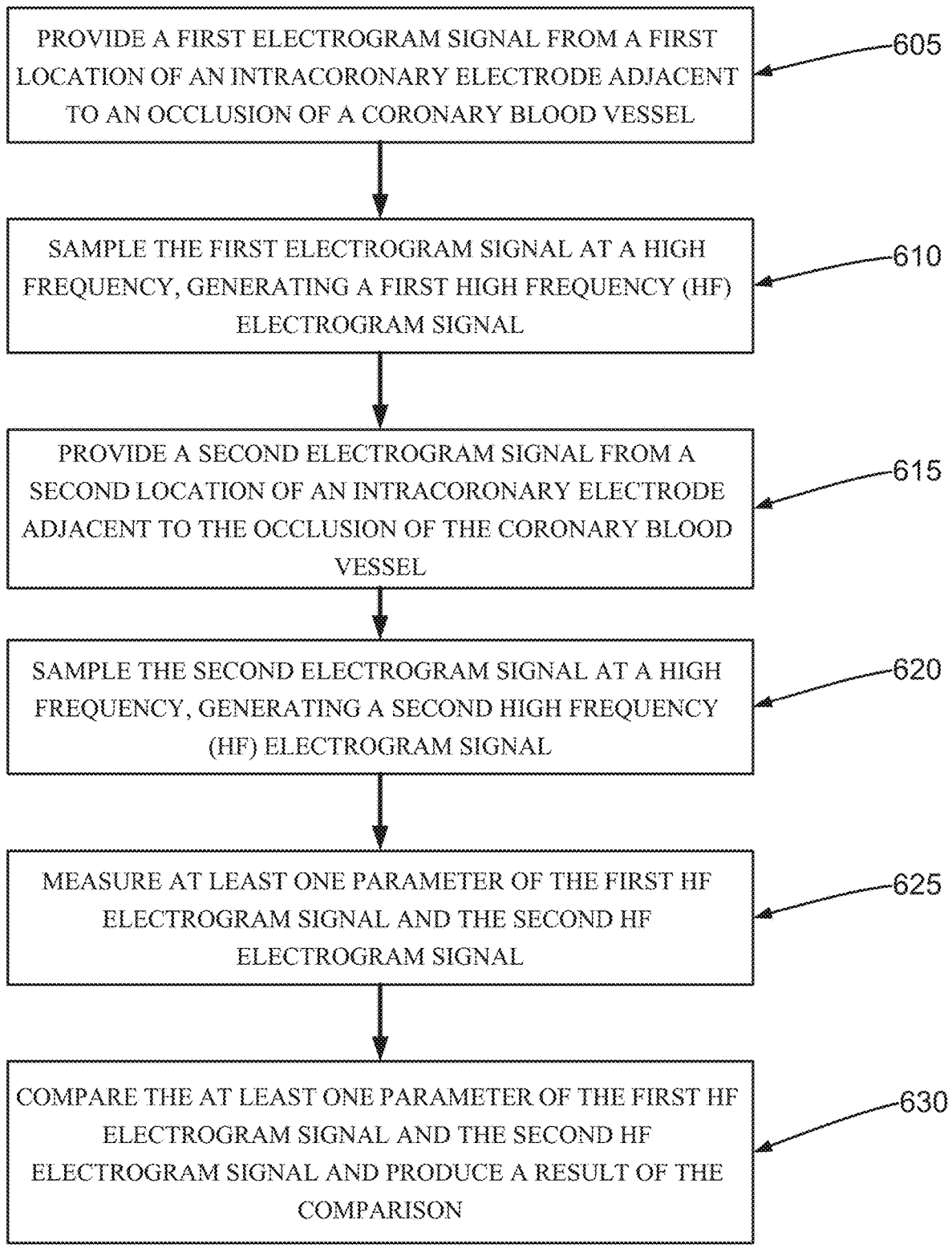
FIG. 6 is a flow chart of a method for analyzing a high frequency (HF) electrogram signal according to an example embodiment of the invention.

Reference is now made to FIG. 6, which is a flow chart of a method for analyzing a high frequency (HF) electrogram signal according to an example embodiment of the invention.

The example embodiment depicted in FIG. 6 includes:

providing a first electrogram signal from a first location of an intracoronary electrode adjacent to an occlusion of a coronary blood vessel (605);

sampling the first electrogram signal at a high frequency, generating a first high frequency (HF) electrogram signal (610);

providing a second electrogram signal from a second location of an intracoronary electrode adjacent to the occlusion of the coronary blood vessel (615);

sampling the second electrogram signal at a high frequency, generating a second high frequency (HF) electrogram signal (620);

having a computer measure at least one parameter of the first HF electrogram signal and the second HF electrogram signal (625); and having the computer compare the at least one parameter of the first HF electrogram signal and the second HF electrogram signal and produce a result of the comparison (630).

In some embodiments, the coronary blood vessel is a coronary artery.

In some embodiments, the coronary blood vessel is a coronary vein, by way of a non-limiting example the coronary sinus.

Figure 7A:
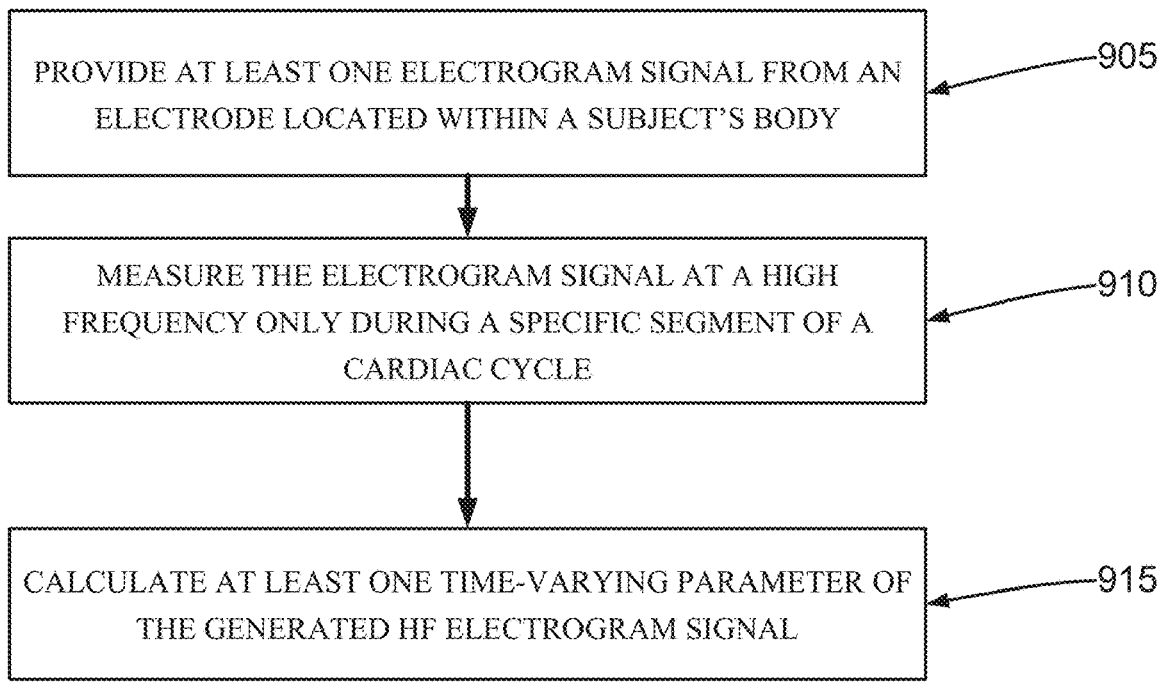
FIG. 7A is a flow chart of a method for analyzing a high frequency (HF) electrogram signal according to an example embodiment of the invention.

Reference is now made to FIG. 7A, which is a flow chart of a method for analyzing a high frequency (HF) electrogram signal according to an example embodiment of the invention.

The example embodiment depicted in FIG. 7A includes:

(a) providing at least one electrogram signal from an electrode located within a subject's body (905);

(b) measuring the electrogram signal at a high frequency only during a specific segment of a cardiac cycle, generating a HF electrogram signal for the specific segment of the cardiac cycle (910); and (c) calculating at least one time-varying parameter of the generated HF electrogram signal (915), in which the specific segment of the cardiac cycle is a one of a group consisting of: a P segment; a Q segment; a R segment; a S segment; a T segment; and a QRS complex.

Figure 7B:
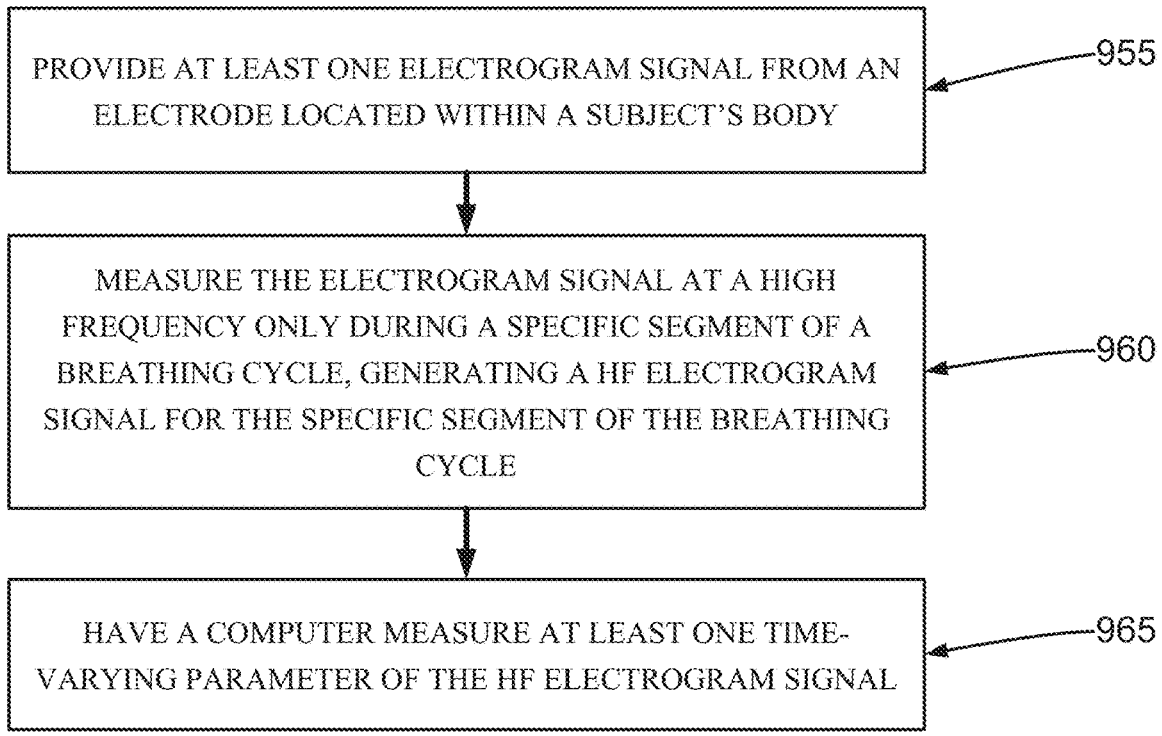
FIG. 7B is a flow chart of a method for analyzing a high frequency (HF) electrogram signal according to an example embodiment of the invention.

Reference is now made to FIG. 7B, which is a flow chart of a method for analyzing a high frequency (HF) electrogram signal according to an example embodiment of the invention.

The example embodiment depicted in FIG. 7B includes:

(a) providing at least one electrogram signal from an electrode located within a subject's body (955);

(b) measuring the electrogram signal at a high frequency only during a specific segment of a breathing cycle, generating a HF electrogram signal for the specific segment of the breathing cycle (960); and (c) having a computer measure at least one time-varying parameter of the HF electrogram signal (970).

Figure 8:
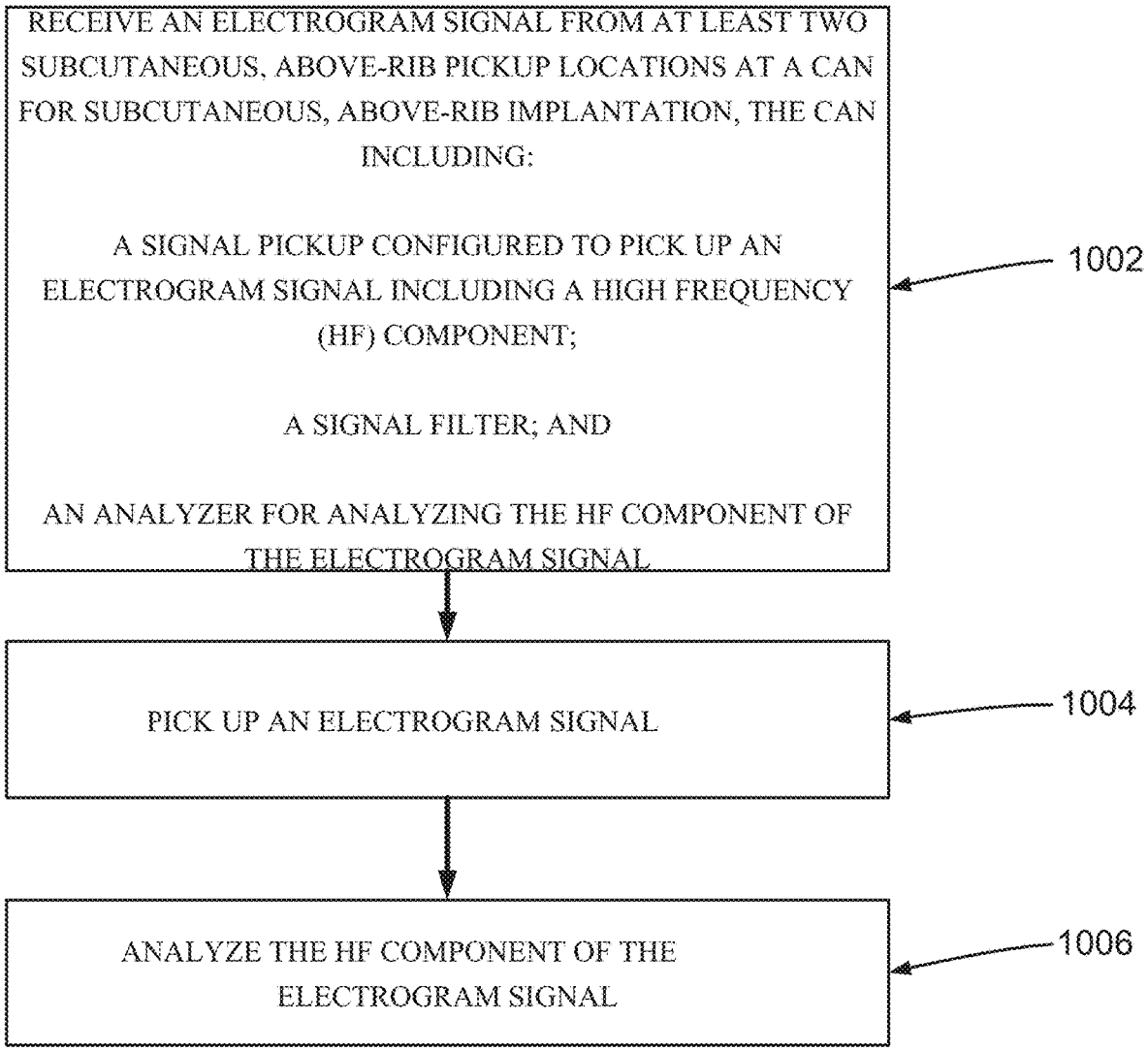
FIG. 8 is a flow chart of a method for analyzing a high frequency (HF) electrogram signal according to an example embodiment of the invention.

Reference is now made to FIG. 8, which is a flow chart of a method for analyzing a high frequency (HF) electrogram signal according to an example embodiment of the invention.

The example embodiment depicted in FIG. 8 includes:

receiving an electrogram signal from at least two subcutaneous, above-rib pickup locations at a can for subcutaneous, above-rib implantation, the can including a signal pickup configured to pick up an electrogram signal including a high frequency (HF) component; a signal filter connected to the signal pickup and configured to measure a high frequency (HF) component from the electrogram signal; and an analyzer for analyzing the HF component of the electrogram signal, wherein the analyzer is configured to analyze at least one time-varying parameter of the HF component of the electrogram signal; and the signal filter is configured to measure the electrogram signal by using a signal picked up from at least two pickup locations (1002).

picking up an electrogram signal (1004); and analyzing the HF component of the electrogram signal (1006).

In some embodiments the at least two subcutaneous, above-rib locations may be located, by way of some non-limiting examples, at:

two electrodes at mid-chest subcutaneous pickup locations;

two electrodes at right-of-sternum subcutaneous pickup locations; and two electrodes at left-of-sternum subcutaneous pickup locations.

In some embodiments the two subcutaneous pickup locations include a subcutaneous, above-rib electrode pickup location and a subcutaneous can pickup location.

In some embodiments the signal pickup is also configured to pick up a low frequency component; the signal filter is also configured to measure the low frequency component from the electrogram signal; and the analyzer is also configured to analyze the low frequency component of the electrogram signal.

In some embodiments the analyzer is configured to analyze three voltage potential difference signals simultaneously, including voltage potential difference signals between the can and a first subcutaneous pickup location; the can and a second subcutaneous pickup location; and the first subcutaneous pickup location and the second subcutaneous pickup location.

In some embodiments the analyzer analyzes the HF component of the electrogram signal and the low frequency component of the electrogram signal simultaneously.

Figure 9:
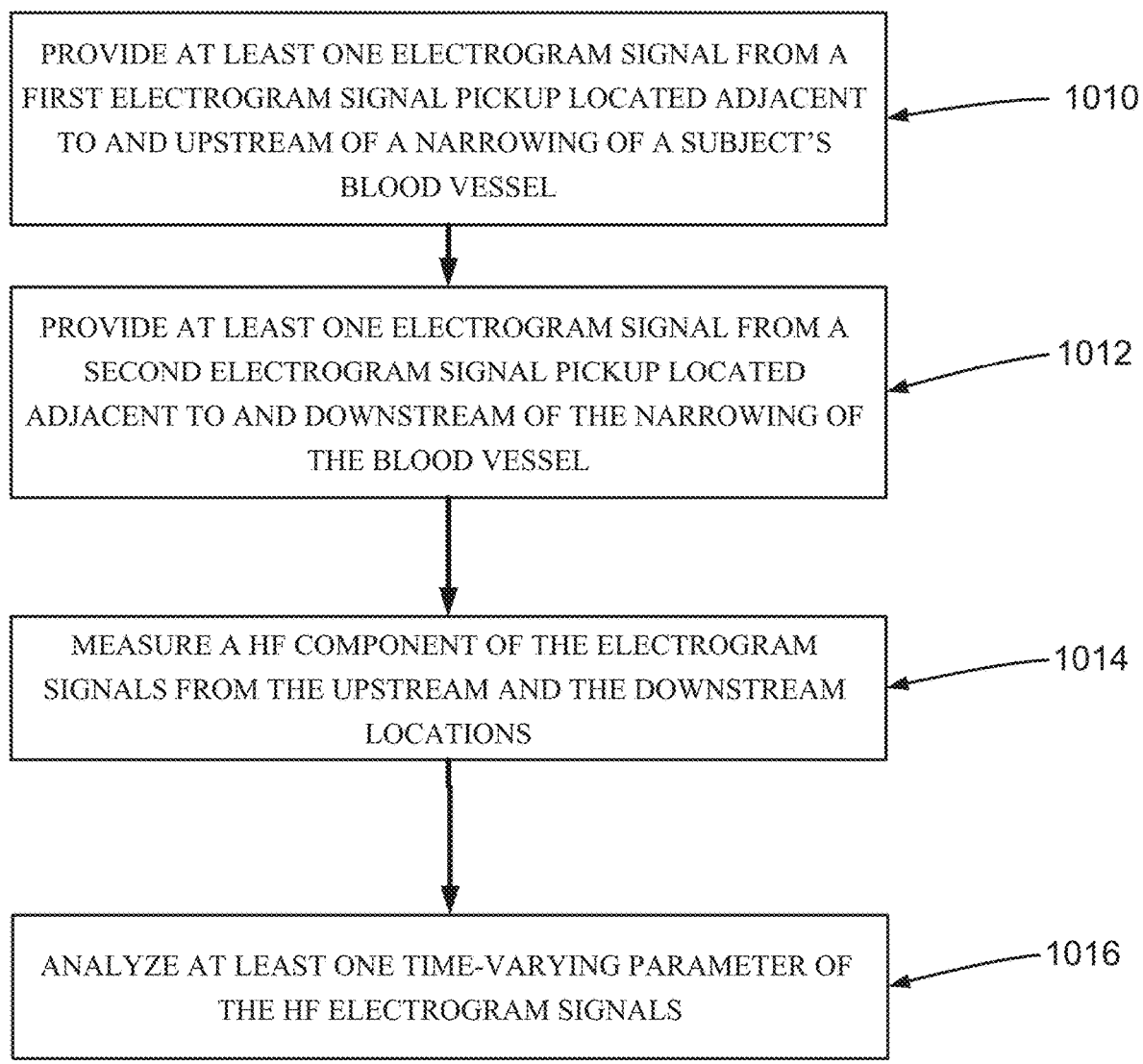
FIG. 9 is a flow chart of a method for analyzing a high frequency (HF) electrogram signal according to an example embodiment of the invention.

Reference is now made to FIG. 9, which is a flow chart of a method for analyzing a high frequency (HF) electrogram signal according to an example embodiment of the invention.

The example embodiment depicted in FIG. 9 includes:

providing at least one electrogram signal from a first electrogram signal pickup located adjacent to and upstream of a narrowing of a subject's blood vessel (1010);

providing at least one electrogram signal from a second electrogram signal pickup located adjacent to and downstream of the narrowing of the blood vessel (1012);

measuring a HF component of the electrogram signals from the upstream and the downstream locations (1014); and analyzing at least one time-varying parameter of the HF electrogram signals (1016).

In some embodiments, the electrogram signals are from an inside of the blood vessel, from a first electrogram signal pickup located within the subject's blood vessel upstream of the narrowing of the blood vessel and from a second electrogram signal pickup located within the subject's blood vessel downstream of the narrowing of the blood vessel.

In some embodiments, the electrogram signals are not necessarily from inside a blood vessel, but rather from a first electrogram signal pickup located outside and adjacent to a subject's blood vessel upstream of a narrowing of the blood vessel and from a second electrogram signal pickup located outside and adjacent to the subject's blood vessel downstream of the narrowing of the blood vessel.

In some embodiments, the electrogram signals from the upstream and the downstream locations are compared to each other.

In some embodiments, a parameter of the electrogram signals from the upstream and the downstream locations which is compared is an amplitude of the HF component of the upstream and the downstream electrogram signals.

In some embodiments, a parameter of the electrogram signals from the upstream and the downstream locations which is compared is an amplitude and/or an RMS amplitude of the HF component of the upstream and the downstream electrogram signals, averaged over a heartbeat, or over several seconds, or over several minutes.

In some embodiments, a parameter of the electrogram signals from the upstream and the downstream locations which is compared is existence of a Reduced Amplitude Zone (RAZ), or a time span of a RAZ.

In some embodiments, following comparison of the electrogram signals from the upstream and the downstream locations, a difference between the signals is optionally considered significant when one signal is reduced, relative to the other, by 5%, 10%, 15%, 25% or even 50%.

In some embodiments, following comparison of the electrogram signals from the upstream and the downstream locations, a difference between the signals is optionally considered significant when one signal is different from the other, by a number of standard deviation units, for example by more than 0.5, 1, 2, 3 standard deviations.

In some embodiments, following comparison of the electrogram signals from the upstream and the downstream locations, a difference between the signals is optionally considered significant when a correlation function between the signals at the 2 location results in a correlation index smaller than 0.98, 0.95, 0.9, 0.8, 0.7, or 0.6.

In some embodiments, when a difference between the signals is considered significant, the significant difference is optionally taken as an indication for ischemia.

In some embodiments, when a difference between the signals is considered significant, the significant difference is optionally taken as an indication for cardiac hibernation.

In some embodiments, the first electrogram signal pickup and the second electrogram signal pickup are in one electrode.

In some embodiments, the first electrogram signal pickup and the second electrogram signal pickup are in separate electrodes.

In some embodiments, at least one of the electrogram signal pickups is a bipolar pickup.

In some embodiments, the first electrogram signal pickup and the second electrogram signal pickup are electrically connected to an electronics unit which communicates wirelessly with an external analyzer, transmitting a signal based on an HF signal picked up by the electrogram signal pickups.

In some embodiments, the electrogram signal from the first electrogram signal pickup and the electrogram signal from the second electrogram signal pickup are measured by the same electrogram signal pickup located upstream of the narrowing of the blood vessel at one time, and downstream of the narrowing of the blood vessel at a different time.

In some embodiments, the above-mentioned analysis includes also FFR (fractional flow reserve) analysis.

In some embodiments, a determination whether stent placement is recommended is based, at least in part, on the analyzing at least one time-varying parameter of the HF electrogram signals and on the FFR (fractional flow reserve) analysis.

In some embodiments, post-revascularization efficacy of revascularization is optionally based, at least in part, on the analyzing at least one time-varying parameter of the HF electrogram signals and on the FFR (fractional flow reserve) analysis.

It is expected that during the life of a patent maturing from this application many relevant electrogram acquisition techniques will be developed and the scope of the term electrogram is intended to include electrograms acquired by all such new technologies a priori.

It is expected that during the life of a patent maturing from this application many relevant wireless transmission techniques will be developed and the scope of the term wireless transmission is intended to include wireless transmission performed by all such new technologies a priori.

It is expected that during the life of a patent maturing from this application many relevant implantable electrodes will be developed and the scope of the term implantable electrodes is intended to include all such new technologies a priori.

As used herein the term "about" refers to ±10%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An implantable device for analyzing a high frequency (HF) electrogram signal received from subcutaneous, above-rib pickup locations, the device comprising:
    an implantable electrode for use inside a living body; and
    a can for subcutaneous implantation, the can comprising:
        a signal pickup configured to pick up an electrogram signal comprising a high frequency (HF) component;
        a signal filter connected to the signal pickup and configured to measure a high frequency (HF) component, at a frequency >105 Hz, from the electrogram signal; and
        an analyzer for analyzing the HF component of the electrogram signal,
    wherein:
    the analyzer is configured to analyze at least one time-varying parameter of the HF component of the electrogram signal;
    the analyzer is configured to provide an alert indicating ischemia based on said analyzing;
    the signal filter is configured to measure said electrogram signal by using a signal picked up from at least two pickup locations which are both subcutaneous and above-rib; and
    said two pickup locations comprise a subcutaneous, above-rib electrode pickup location and a can pickup location.

2. The device of claim 1 in which:
    said signal pickup is also configured to pick up a low frequency component;
    said signal filter is also configured to measure said low frequency component from the electrogram signal; and
    said analyzer is also configured to analyze the low frequency component of the electrogram signal.

3. The device of claim 1 in which said analyzer is configured to analyze three voltage potential difference signals simultaneously, the three voltage potential difference signals comprising voltage potential difference signals between said can and a first subcutaneous pickup location; said can and a second subcutaneous pickup location; and said first subcutaneous pickup location and said second subcutaneous pickup location.

4. The device of claim 2 in which said analyzer is configured to analyze said HF component of the electrogram signal and said low frequency component of the electrogram signal simultaneously.

5. A method for analyzing a high frequency (HF) electrogram signal comprising:
    receiving an electrogram signal from at least two subcutaneous, above-rib pickup locations at a can for subcutaneous, above-rib implantation, the can comprising:
        a signal pickup configured to pick up an electrogram signal comprising a high frequency (HF) component at a frequency >105 Hz;
        a signal filter connected to the signal pickup and configured to measure a high frequency (HF) component from the electrogram signal; and
        an analyzer for analyzing the HF component of the electrogram signal,
    wherein:
    the analyzer is configured to analyze at least one time-varying parameter of the HF component of the electrogram signal; and
    the signal filter is configured to measure said electrogram signal by using a signal picked up from at least two pickup locations, wherein said two pickup locations comprise a subcutaneous, above-rib electrode pickup location and a can pickup location;
    picking up said electrogram signal;
    analyzing said HF component of the electrogram signal; and
    providing an alert indicating ischemia based on said analyzing.

6. The method of claim 5 in which said at least two subcutaneous, above-rib pickup locations comprise two subcutaneous, above-rib, pickup locations selected from a group consisting of:
two electrodes at mid-chest pickup locations;
two electrodes at right-of-sternum pickup locations; and
two electrodes at left-of-sternum pickup locations.

7. The method of claim 5 in which:
said signal pickup is also configured to pick up a low frequency component;
said signal filter is also configured to measure said low frequency component from the electrogram signal; and
said analyzer is also configured to analyze the low frequency component of the electrogram signal.

8. The method of claim 5 in which said analyzer is configured to analyze three voltage potential difference signals simultaneously, and the three voltage potential difference signals comprise voltage potential difference signals between said can and a first subcutaneous pickup location; said can and a second subcutaneous pickup location; and said first subcutaneous pickup location and said second subcutaneous pickup location.

9. The method of claim 7 in which said analyzer analyzes said HF component of the electrogram signal and said low frequency component of the electrogram signal simultaneously.

10. The device of claim 1 in which said implantable electrode comprises at least two implantable electrodes configured to extend from the can to at least two subcutaneous, above-rib pickup locations selected from a group consisting of:
two electrodes at mid-chest pickup locations;
two electrodes at right-of-sternum pickup locations; and
two electrodes at left-of-sternum pickup locations.

11. The device of claim 1 and further comprising a signal filter arranged to start measuring said electrogram signal a specific period of time following a synchronizing pacing signal.

12. The method of claim 5 wherein the signal pickup is arranged to start picking up said electrogram signal at a high frequency during a specific segment of a breathing cycle.

13. The method of claim 5 wherein the analyzing comprises analyzing only when a correlation coefficient value of the generated HF electrogram signal to a template is larger than a threshold value.

14. The method of claim 5 wherein the analyzing comprises comparing a value of the time-varying parameter of the HF electrogram signal and a prior value of the time-varying parameter of the HF electrogram signal under same heart rate conditions, the same conditions selected from a group consisting of
(a) same heart rate;
(b) same heart rate increase;
(c) same heart rate decrease; and
(d) same pattern of change of heart rate.

15. The method of claim 5 wherein the signal pickup is arranged to start picking up said electrogram signal a specific period of time following a synchronizing pacing signal.

16. The method of claim 5 wherein the signal filter is arranged to measure the electrogram signal only during a specific portion of a cardiac cycle, wherein the specific portion of the cardiac cycle is a P segment; and the analyzer is configured to provide indication of atrial arrhythmia, and further comprising manipulating a pacing rate, based on the indication, to overcome the atrial arrhythmia.

17. The method of claim 5 wherein the signal filter is arranged to measure the electrogram signal only during a specific portion of a cardiac cycle, the specific portion of the cardiac cycle is a QRS complex; and the analyzer is configured to provide indication of onset of an ischemic event, and further comprising manipulating a pacing rate, based on the indication, to overcome the onset of the ischemic event by reducing the pacing rate.

18. The method of claim 5 wherein the signal filter is arranged to measure the electrogram signal only during a specific portion of a cardiac cycle, the specific portion of the cardiac cycle is a P segment, and the analyzing is used to provide warning of a condition selected from a group consisting of:
an irregular propagation of an action potential in a cardiac atria;
atrial tachycardia;
atrial bradycardia; and
atrial arrhythmia.

19. The method of claim 5 in which the subcutaneous, above-rib electrode pickup location is on a left edge of a subject's sternum or in a subject's thorax.

20. The implantable device of claim 1 in which the implantable electrode for use inside a living body comprises an implantable bipolar electrode.

* * * * *